United States Patent [19]

Speckamp et al.

[11] Patent Number: 5,079,257

[45] Date of Patent: Jan. 7, 1992

[54] INDOLOQUINONE COMPOUNDS

[76] Inventors: Willem N. Speckamp; Everardus A. Oostveen, both of Laboratory of Organic Chemistry, University of Amsterdam, Nieuwe Achtergracht, Amsterdam, Netherlands

[21] Appl. No.: 278,531

[22] PCT Filed: Apr. 15, 1987

[86] PCT No.: PCT/GB87/00253

§ 371 Date: Nov. 23, 1988

§ 102(e) Date: Nov. 23, 1988

[87] PCT Pub. No.: WO87/06227

PCT Pub. Date: Oct. 22, 1987

[30] Foreign Application Priority Data

Apr. 17, 1986 [GB] United Kingdom ............... 8609369
Jun. 24, 1986 [GB] United Kingdom ............... 8615383
Dec. 4, 1986 [GB] United Kingdom ............... 8629049

[51] Int. Cl.$^5$ ............... A01N 43/90; A61K 31/47; C07D 209/32; C07D 209/46
[52] U.S. Cl. ............... 514/312; 548/512
[58] Field of Search ............... 548/512; 514/312

[56] References Cited

U.S. PATENT DOCUMENTS 3,265,698 8/1966 Allen, Jr. et al. ............... 260/268

FOREIGN PATENT DOCUMENTS 1087325 10/1967 United Kingdom .

Primary Examiner—Robert A. Wax
Assistant Examiner—F. Tsung
Attorney, Agent, or Firm—Walter C. Farley

[57] ABSTRACT

Indoloquinone compounds useful as cytostatic agents have formula (I), where $R_2$ and $R_3$ are in each case, hydrogen, halogen, an alkyl group (which may be substituted), an alkoxy group or an aryloxy group, an alkylthio group or an arylthio group, a primary or secondary amino group, hydroxy group or an amino group; $R_5$ is hydrogen, a hydroxy group, an alkoxy group, an alkyl group (which may be substituted), or a carbohydrate moiety; $R_6$ and $R_7$ are in each case hydrogen, halogen, or an alkyl group; $R_8$ is a group —$CH_2X_1$, a group —$CO_2$—$M^+$, where $M^+$ is a metal ion; a group —$CO_2R_{10}$, where $R_{10}$ is hydrogen or an alkyl group (which may be substituted); a group —CONR'R", where R' and R" are hydrogen or alkyl groups (which may be substituted); $R_9$ is a group —$CR_{11}R_{12}X_2$, a group —$CO_2$—$M^+$, where $M^+$ is a metal ion; a group —$CO_2R_{13}$, where $R_{11}$, $R_{12}$ and $R_{13}$ are in each case hydrogen or an alkyl group (which may be substituted); a group —CONR'R", where R' and R" are in each case hydrogen or an alkyl group (which may be substituted), and $X_1$ and $X_2$ (when present) are hydrogen, or groups selected from OH, OR, —OC=OR, —$OCO_2R$, —OC=ONRR, SH, SR, —SC=OR, —SC=SR, —$SCO_2R$, —SC=SOR, —SC—ONRR, —SC—SNRR, and —NRR [where R is hydrogen, an alkyl group (which by be substituted), or an aryl group (which may be substituted)], —OSOR, —$OSO_2R$ and $OP(OR)_2$ [where R is hydrogen, an alkyl group (which may be substituted,), an aryl group (which may be substituted), or a carbohydrate moiety]; and $X_1$ and $X_2$ may be the same or different. Preferred compounds and methods for their manufacture are provided.

4 Claims, No Drawings

INDOLOQUINONE COMPOUNDS

The present investigation relates to new indoloquinone compounds and to methods of preparing them.

Mitomycins[1] have been known for many years to have strong antibacterial and cytostatic activity. In particular, mitomycin C, which has the formula:

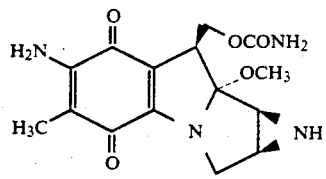
(1)

has been shown to be active against breast, pancreatic and prostatic adenocarcinomas, and notably against colon, bladder, lung and gastro-intestinal cancer.

However, clinically, mitomycin C was found to have disadvantages and consequently many derivatives of mitomycin C have been synthesized in attempts to develop more effective antitumour agents with a higher antitumour activity and a lower toxicity than mitomycin C itself.

Among the derivatives of mitomycin C, 7-methoxymitosene of the formula:

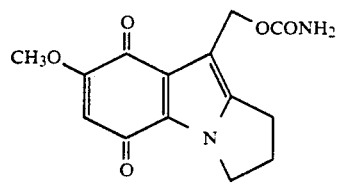
(2)

is known to have important antibacterial activity in vitro and in mice[2], and this fact prompted the synthesis of a number of related indoloquinones of the general formula[3]:

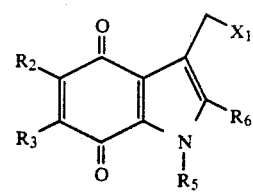
(3)

These compounds were found to have antibacterial activity, but none show antitumour activity below the toxic dosis. However the degree of variation in the structure of indoloquinones produced was limited by the method of synthesis used.

The mitomycin antibiotics belong together with the anthracyclines[4], the aziridinyl quinones[5], streptonigrin[6], saframycin[7] and mitoxanthrone[8] to the quinoid antitumour compounds[9], which require reduction to exert their main cytotoxic effects. The following two mechanisms of action may be involved:

A. Redox cycling[10].
B. Bioreductive alkylation[11].

A. Redox cycling (Scheme 1 A)

Quinoid cytostatic agents are transformed by an enzymatic one-electron reduction into their corresponding semiquinone radical anions. Because of its ubiquitous existance in many cells and cell compartments NADPH-cytochrome P-450 reductase is regarded as the major enzyme catalyzing these reactions. Depending on the redox potential of the semiquinone radical anion, a reaction with oxygen may occur. The superoxide anion formed can undergo a variety of reactions. It spontaneously dismutates to hydrogen peroxide and singlet oxygen ($^1O_2$). Ground state dioxygen is formed when superoxide dismutase is involved in this step. Superoxide anion radicals together with hydrogen peroxide molecules give rise to the formation of cytotoxic hydroxyl radicals in the metal-catalyzed Haber-Weiss cycle.

Scheme 1A

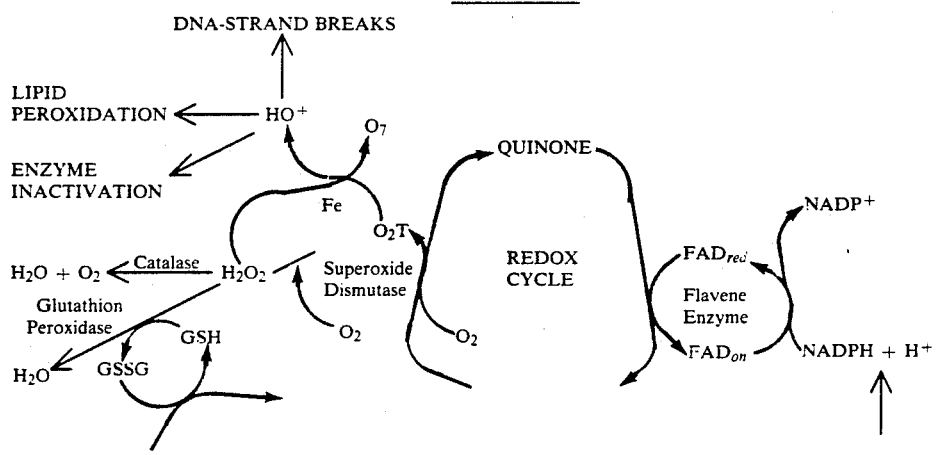

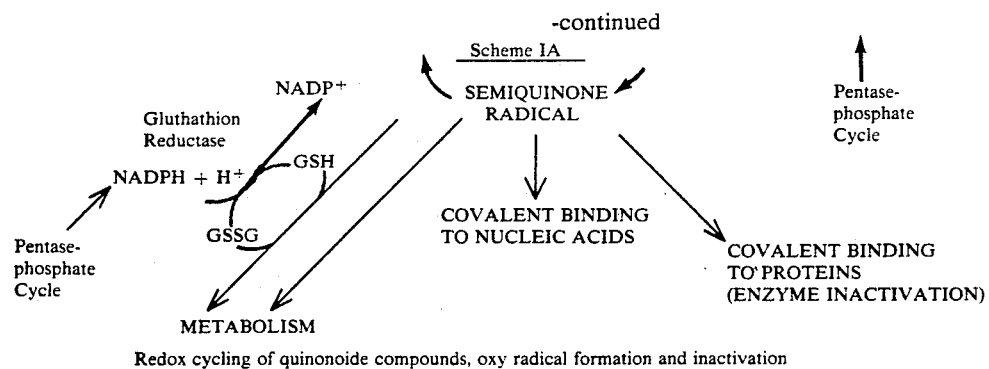

Redox cycling of quinonoide compounds, oxy radical formation and inactivation

Haber-Weiss equation

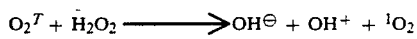

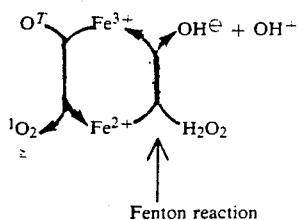

Fenton reaction

The hydroxyl radical, the most reactive oxygen metabolite, is suggested to be responsible for some of the serious damages occurring during redox cycling processes, e.g. lipid peroxidation, enzyme inactivation and DNA cleavage. Further as can be derived from scheme 1 A, NADPH depletion could also be a critical event.

Tumour cells are deficient in enzymes that normally protect the cell against free radical damage and this may explain part of the selective cytotoxicity of the antitumour quinones[12]. The protective mechanism embraces a combined action of either superoxide dismutase and catalase or superoxide dismutase and glutathion peroxidase.

B. Bioreductive alkylation

Several reduced quinoid cytostatic agents are not stable, but decompose into reactive intermediates which can undergo nucleophilic addition reactions with several biologically important nucleophiles.

The concept of "bioreductive alkylation", which applies to the mechanism of action of these antitumour compounds, has been formulated by Lin et al. in 1972[11a], on studying the biological activity of derivatives of methyl substituted benzoquinones and naphthoquinones. The bioreductive activation of quinone containing cytostatic agents in essence comprises the reduction of quinone (4) to its dihydroform (5) after which HX is expelled and the α-methylene carbonyl structure (6) generated. The latter form supposedly acts as a Michael acceptor and binds the nucleophile (Scheme 1 B).

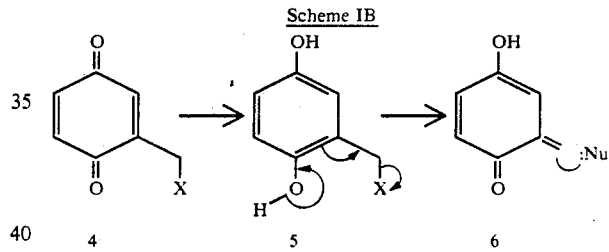

The efficiency of such compouds can be enhanced by the introduction of additional methyl substituents bearing a leaving group. Upon reductions two or more unsaturated moieties are formed, creating possibilities for the crosslinking of DNA molecules (Scheme 1 C). In this way the antitumour activity of the quinoid compound will be reinforced.

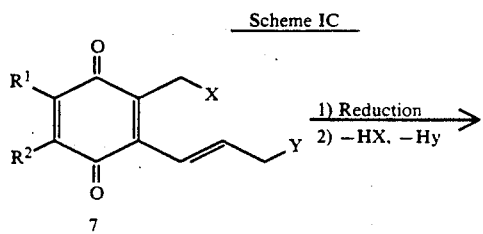

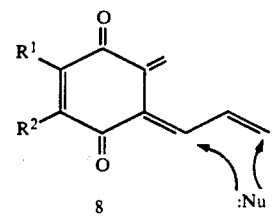

Bioreductive alkylating indoloquinones have become of increasing importance, since they might act as selective chemotherapeutics for hypoxic cells[13]. These malignant cells, which form part of the slowly growing solid tumours, provide a more efficient reducing environment then do oxygen rich tumour or normal cells. So the reductive activation of the quinone-hydroquinone type may proceed more effectively.

The concept of bioreductive alkylation is of potential major significance as a mechanism of action of the mitomycins, anthracyclines and aziridinyl quinones. They are reductively activated by the uptake of both one as well as two electrons.

The molecular mechanism of action of the mitomycin (1) antibiotics has been studied extensively the last five years[14]. The reactive intermediates (10–12) which arise upon reductive activation are given in FIG. 1[15,16].

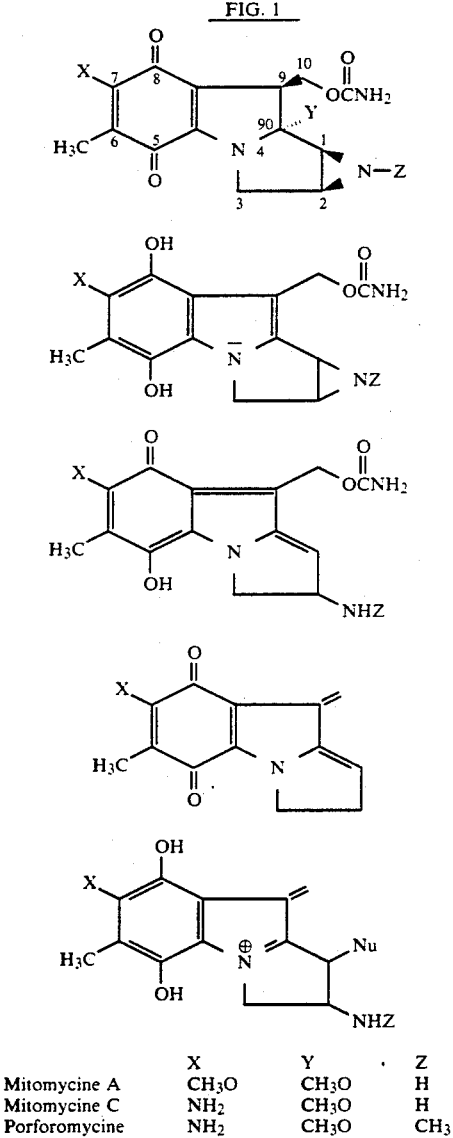

|  | X | Y | Z |
|---|---|---|---|
| Mitomycine A | CH$_3$O | CH$_3$O | H |
| Mitomycine C | NH$_2$ | CH$_3$O | H |
| Porforomycine | NH$_2$ | CH$_3$O | CH$_3$ |

It has been well established, that mitomycin C (MMC), the prototype of this class of anticancer drugs, either upon chemical or enzymatical reduction, may bind via its C-1 atom covalently to suitable nucleophiles (e.g. DNA or DNA)[15]. It has also been observed, that MMC acts as a bisalkylating agent via its C-1 and C-10 carbon atom[16]. On interaction with DNA crosslinked adducts are formed in this manner. Whether mono- or bis-alkylation occurs is strongly dependent on the reducing conditions, the nature of the nucleophiles and the environmental pH. Crosslinking of DNA with protein by reductively activated Mitomycin C has been reported[17]. Recent studies by Dorr et al.[18] conducted in mamalian tumour cell cultures, indicated that mitomycin C caused rapid DNA instrand crosslinks in a dose dependent fashion. Good correlations between DNA crosslinks and cytotoxicity have also been reported[18,19]. The chemical structures of monofunctionally linked adducts obtained upon catalytically hydrogenation of MMC in the presence of calf thymus DNA were reported by Hashimoto et al.[15d,e]. Three modified nucleophiles were obtained: C-1 alkylation products of MMC with the O-6 and N-2 positions of guanine, and the N-6 position on adenine. Pan et al.[20] reported the alkylation of DNA after anaerobic reductive activation of mitomycin C by NADPH cytochrome P-450 reductase and xanthine oxidase. The preferential site for monofunctional binding was found to be the O-6 position of guanine. This in contrast to the results obtained during catalytically hydrogenation, showing the influence of the reduction conditions on the site of alkylation of DNA.

The first steps in the molecular activation sequence of MMC comprise its conversion into hydroquinone 9[11c,21]. The latter intermediate is structurally related to intermediates arising from the mitosenes[22] after reductive activation. The driving force for the activation of the C-1 position in preference to the C-10 position in MMC has to ascribed to the opening of the aziridine ring thereby releasing the strain energy during the formation of quinon methide 10. Activation of the second electrophilic center (C-10) may take place via one of the following two ways: i. Conversion of the monoquinone methide 10 into bisquinone methide 11 via elimination of the elements of HOCONH$_2$. ii. Nucleophilic trapping of quinone methide 10 and elimination of HOCONH$_2$ from the resulting adduct affording iminium derivative 12, which may act as both an electrophilic or a nucleophilic trap. Hornemann c.s.[16a] and recently Kohn c.s.[23] have presented evidence favouring the iminium pathway. Finally the dual reactivity of quinone methide 10 has also unequivocally been established[15a,g,24]. Very recently, M. R. Bachur et al. have demonstrated, using electrochemical techniques, that a one-electron reduction of the drug suffices to activate it[25]. Previously this group[26] and also others[27] have presented unambiguous E.S.R. evidence for the enzymetically generated semiquinone metabolite of Mitomycine C. Bachur et al.[26] proposed that mitomycine C undergoes primary molecular activation in the cell under anaerobic conditions via flavoenzyme single electron transfer to the quinone nucleus. The resulting radical anion produces monofunctional adducts with DNA and other nucleophiles, which can undergo secondary flavoenzyme activation leading to a new anaerobic free radical. Via this secondary activation, monofunctional adducts may be converted into bifunctional adducts e.g. crosslinked DNA.

A different mechanism operating under aerobic conditions is the formation of reactive oxygen species produced by redox cycling. When Mitomycin C was incubated with supercoiled covalently closed circular (CCC) DNA and a reducing agent in the presence of oxygen it produced single strand breaks[28]. Strand breaking of circular DNA by reduced mitomycin is oxygen-dependent and is inhibited by catalase, by superoxide dismutase and by free radical scavengers. The formation of hydroxyl radicals during reduction of mitomycin C by NADPH cytochrome P-450 reductase and xanthine oxidase under aerobic conditions has been reported[29,30], as well as the formation of both superoxide anion and hydroxyl radicals in tumour cells[30]. The lethal action of mitomycin C—in particular the toxicity—can be partly correlated to the generation of reactive oxygen species.

REFERENCES

1a. W. A. Remers, The Chemistry of Antitumour Antibiotics, Vol. 1, John Wiley & Sons, New York 1979, Ch. 5, p 221.
1b. S. K. Carter and S. T. Crooke (Eds), Mitomycin C—Current Status and New developments, Academic Press, New York (1979).
1c. M. Ogawa, M. Rosenczweig and M. J. Staquet (Eds), Mitomycin C—Current Impact on Cancer Chemotherapy, Excerpta Medica, Princeton, Genova, Tokyo (1982).
2. C. R. Allen, Jr., J. F. Poletto, M. J. Weiss, J. Amer. Chem. Soc., 86, 3877 (1964).
3. M. J. Weiss, G. S. Redin, G. R. Allen, Jr., A. C. Dornbush, H. L. Lindsay, J. F. Poletto, W. A. Remers, R. H. Roth and A. E. Sloboda, J. Med. Chem., 11, 742 (1968).
4a. F. Arcamone, Doxorubicin Anticancer Antibiotics, Academic Press, New York (1981).
4b. F. Arcamone, Med. Res. Rev., 1984, Vol. 4, 153.
5. J. S. Driscoll in "Structure-Activity Relationships of Anti-Tumour Agents, D. N. Reinhoudt, T. A. Connors, H. M. Pinedo asnd K. W. van der Poll (Eds.)", Martinus Nijhoff Publishers, The Hague (1983).
5b. M. Yoshimoto, H. Miyazawa, H. Nakao, K. Shinkai and M. Arakawa, J. Med. Chem., 22, 491 (1979).
6. I. A. Shaikh, F. Johnson and A. P. Grollman, J. Med. Chem., 29, 1329 (1986).
7a. T. Arai, K. Takahashi and A. Kabo, J. Antibiot., 30, 1015 (1977).
7b. J. W. Lown, A. V. Joshua and J. S. Lee, Biochem., 1982, (3), 419.
8a. I. E. Smith, Cancer Treat. Rev., 10, 103 (1983)
8b. C. C. Cheng, R. K-Y. C-Cheng, Progr. Med. Chem., 20, 83 (1983).
9. J. W. Lown, Adv. Free Rad. Biol. & Med., Vol. 1, pp 225–264 (1985).
10. H. Kappus, Biochem. Pharmac., 35, 1 (1986).
11a. A. J. Lin, L. A. Cosby, C. W. Shansky and A. C. Sartorelli, J. Med. Chem., 15, 1247 (1972).
11b. H. W. Moore and R. Czerniack, Med. Res. Rev., 1, 249 (1981).
11c. H. W. Moore, Science, 197, 527 (1977).
12a. G. Powis, B. A. Svingen and P. Appel, Mol. Pharmac., 20, 387 (1981).
12b. L. W. Oberlay (Ed.) Superoxide dismutase, Vol. 2, CRS Press, Florida (1982).
13a. K. A. Kennedy, B. A. Teicher, S. Rockwell and A. C. Sartorelli, Biochem. Pharmac., 29, 1 (1980).
13b. A. C. Sartorelli, Biochem. Pharmac., 35, 67 (1986).
13c. W. A. Wenny and W. R. Wilson, J. Med. Chem., 29, 879 (1986).
14. S. Stinson, Chem. & Eng. News, Sept. 1986, 26.
15a. M. Tomasz and R. Lipman, Biochem., 20, 5056 (1981).
15b. M. Tomasz, M. Jung, G. Verdine and K. Nakanishi, J. Amer. Chem. Soc., 106, 7367 (1984).
15c. Y. Hashimoto, K. Shudo and T. Okamoto, Chem. Pharm. Bull., 28, 1961 (1980).
15d. Y. Hashimoto, K. Shudo and T. Okamoto., Tetrahedron lett., 23, 677 (1982).
15e. Y. Hashimoto, K. Shudo and T. Okamoto., Acc. Chem. Res., 17, 403 (1984).
15g. D. M. Peterson and J. Fisher, Biochem., 25, 4077 (1986).
16a. U. Hornemann, P. J. Keller and J. F. Kozlovski, J. Amer. Chem. Soc., 101 7121 (1979).
16b. U. Hornemann, K. Iguchi, P. J. Keller, H. M. Vu; J. F. Kozlowski and H. Kohn, J. Org. Chem., 48, 5026 (1983).
16c. M. Bean and H. Kohn, J. Org. Chem., 48, 5033 (1983).
16d. M. Bean and H. Kohn, J. Org. Chem., 50, 293 (1985).
17. R. E. Meyn, S-F. Jenkins and L. H. Thompson, Cancer Res., 45, 3510 (1985).
18. R. T. Dorr, G. T. Bowden, D. S. Alberts and J. D. Liddil, Cancer Res., 45, 3510 (1985).
19. K. A. Kennedy, J. D. Gurl, L. Leondaris and D. Alabaster, Cancer Res., 45, 3541 (1985).
20. S. S. Pan, T. Iracki and N. R. Bachur, Mol. Pharmac., 29, 622 (1986).
21a. S. J. Danishefsky and M. Ciufolini, J. Amer. Chem. Soc., 106, 6424 (1984).
21b. S. J. Danishefsky and M. Egbertsen, J. Amer. Chem. Soc., 108, 4648 (1986).
22a. W. S. Taylor, G. Leadbetter, D. L. Fost and W. A. Remers, J. Med. Chem., 20, 138 (1977).
22b. J. C. Hodges and W. A. Remers, J. Med. Chem., 24, 1184 (1981).
22c. M. L. Casner, W. A. Remers and W. T. Bradner, J. Med. Chem., 28, 921 (1985).
23. N. Zein and H. Kohn, J. Amer. Chem. Soc., 108, 296 (1986).
24. H. Kohn and N. Zein, J. Amer. Chem. Soc., 105, 4105 (1983).
25. P. A. Andrews, S. S. Pan and N. R. Bachur, J. Amer. Chem. Soc., 108, 4158 (1986).
26. S. S. Pan, P. A. Andrews and C. J. Glover, J. Biol. Chem., 259 (2), 959 (1984).
27. B. Kalyanaraman, E. Pere-Reyes and P. R. Mason, Biochim. Biophys. Acta, 630, 119 (1980).
28. J. W. Lown, Mol. Cellular biochem., 55, 17 (1983).
29. T. Komigama, T. Kikuchi and Y. Suyiera, Biochem. Pharmac., 31 (22), 3651 (1982).
30. C. A. Pritsos and A. C. Sartorelli, Cancer Res., 46, 3528 (1986).

For the synthesis of mitomycin analogues having improved antibacterial and cytostatic activity, the present Applicants have been concerned with the following requirements:

(i) The presence of a quinone ring is essential, and by varying the substituents of the benzoquinone ring, the reduction potential of the molecule and consequently the selectivity of the bioreductive alkylating cytostatic agent can be directed.

(ii) The analogue has to contain one or two leaving groups attached either to C-1 and/or C-10, or to carbon atoms in vinylogous positions to C-1 or C-10.

(iii) The lipophilicity of the molecule as a whole can be controlled by the introduction of additional substituents.

The present Applicants have developed synthesis methods which can be used to prepare indoloquinones of more varied structure fulfilling these requirements, and it is an object of the present invention to provide indoloquinones which have improved antibacterial and cytostatic activities at non-toxic dosages.

According to a first aspect of the invention, there are provided indoloquinone compounds of the general formula:

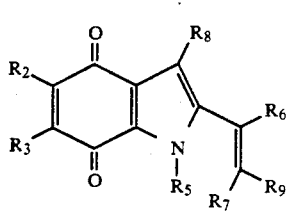
(I)

where

R$_2$ and R$_3$ are in each case, hydrogen, halogen, an alkyl group (which may be substituted), an alkoxy group or an aryloxy group, an alkylthio group or an arylthio group, an primary or secondary amino group, an hydroxy or an amino group;

R$_5$ is hydrogen, an hydroxy group, an alkoxy group, an alkyl group (which may be substituted), or a carbohydrate moiety;

R$_6$ and R$_7$ are in each case hydrogen, halogen, or an alkyl group;

R$_8$ is a group —CH$_2$X$_1$, a group —CO$_2^-$M$^+$, where M$^+$ is a metal ion; a group —CO$_2$R$_{10}$, where R$_{10}$ is hydrogen or an alkyl group (which may be substituted); a group —CONR'R", where R' and R" are hydrogen or alkyl groups (which may be substituted);

R$_g$ is a group —CR$_{11}$R$_{12}$X$_2$, a group —CO$_2^-$M$^+$, where M$^+$ is a metal ion; a group CO$_2$R$_{13}$, where R$_{11}$, R$_{12}$ and R$_{13}$ are in each case hydrogen or an alkyl group (which may be substituted); a group —CONR'R", where R' and R" are in each case hydrogen or an alkyl group (which may be substituted); and X$_1$ and X$_2$ (when present) are hydrogen, or groups selected from —OH, —OR, —OC=OR, —O-CO$_2$R, —OC=ONRR, —SH, SR, —SC=OR, —SC$_2$R, —SC=SR, —SCO$_2$R, —SC=SOR, —SC=ONRR, —SC=SNRR, and —NRR [where R is hydrogen, an alkyl group (which may be substituted), or an aryl group (which may be substituted)], —OSOR, —OSO$_2$R and OP(OR)$_2$ [where R is hydrogen, an alkyl group (which may be substituted), an aryl group (which may be substituted), or a carbohydrate moiety];

and X$_1$ and X$_2$ may be the same or different.

According to a further aspect of the invention preferred bioreductive alkylating indoloquinone compounds are compounds of the general formula:

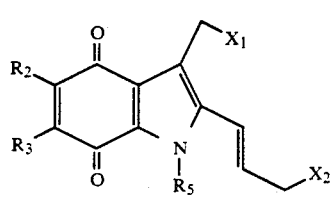
(II)

where

R$_2$ is a methoxy group —OCH$_3$, or a primary or secondary amino group;

R$_3$ is hydrogen or a methyl group; R$_5$ is a methyl group or a butyl group.

X$_1$ and X$_2$ are selected from hydrogen, —OH, —OAc, —OCOOCH$_3$, —CONH$_2$, —O-CONHCH$_2$CH$_2$Cl, —OCOC$_6$H$_5$, —OCOC$_4$H$_9$, —NHC$_6$H$_5$, —SC=SOC$_2$H$_5$ and —OCH$_3$ and may be the same or different.

Particularly preferred bioreductive alkylating indoloquinone compounds according to the invention are:

(1) 3-Acetoxymethyl-5-methoxy-1-methyl-2-[1H-indole-4,7-dione]prop-β-en-α-yl acetate (Compound E.O. 1)

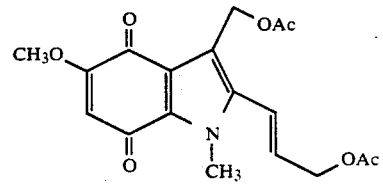

(1A) 3-Hydroxymethyl-5-methoxy-1-methyl-2-[1H-indole-4,7-dione]prop-β-en-α-yl acetate (Compound E.O. 1A)

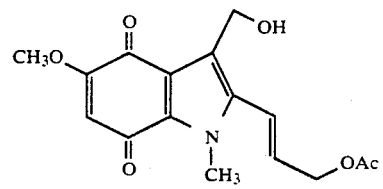

(1B) 3-Acetoxymethyl-5-methoxy-1-methyl-2-[1H-indole-4,7-dione]prop-β-en-α-ol (Compound E.O. 1B)

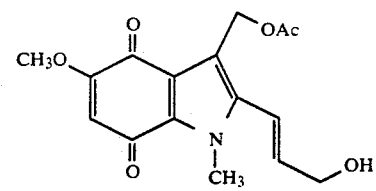

(2) Methyl 5-methoxy-3-methoxycarbonyloxymethyl-1-methyl-2-[1H-indole-4,7 dione]prop-β-en-α-yl carbonate (Compound E.O. 2)

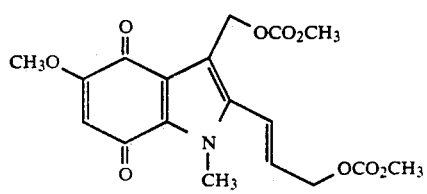

(3) 3-Carbamoyloxymethyl-5-methoxy-1-methyl-2-[1H-indole-4,7-dione]prop-β-en-α-yl carbamate (Compound E.O. 3)

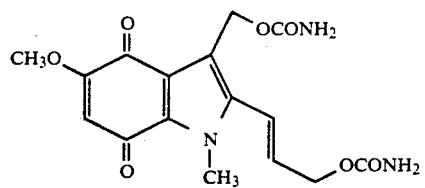

(4) 3-Acetoxymethyl-5-aziridino-1-methyl-2-[1H-indole-4,7-dione]prop-β-en-α-yl acetate (Compound E.O. 4)

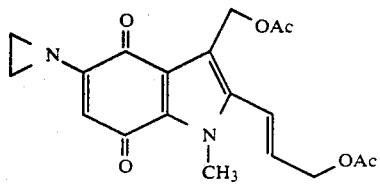

(4A) 3-Acetoxymethyl-5-aziridino-1-methyl-2-[1H-indole-4,7-dione]prop-β-en-α-ol (Compound E.O. 4A)

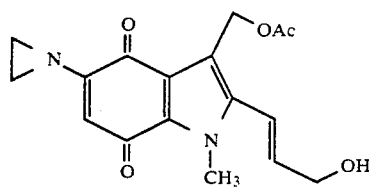

(5) 3-Acetoxymethyl-5-(2-hydroxyethyl-1-amino)-1-methyl-2-[1H-indole-4,7-dione]prop-β-en-αyl acetate (Compound E.O. 5)

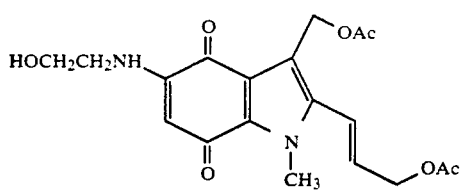

(6) 3-Acetoxymethyl-5-(2,3-dihydroxypropyl-1-amino)-1-methyl-2-[1H-indole-4,7-dione]prop-β-en-α-yl acetate (Compound E.O. 6)

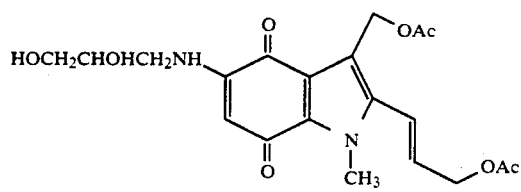

(7) 3-Hydroxymethyl-5-methoxy-1-methyl-2-[1H-indole-4,7-dione]prop-β-en-α-ol (Compound E.O. 7)

E.O.3

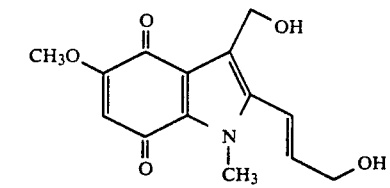

(8) 3-Hydroxymethyl-1-methyl-5-propyleneamino-2-[1H-indole-4,7-dione]prop-β-en-α-ol (Compound E.O. 8)

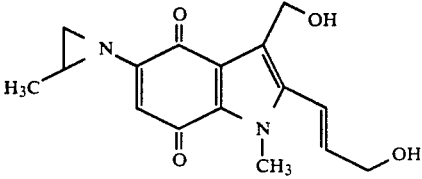

(9) 5-Aziridino-3-hydroxymethyl-1-methyl-2-[1H-indole-4,7-dione]prop-β-en-α-ol (Compound E.O. 9)

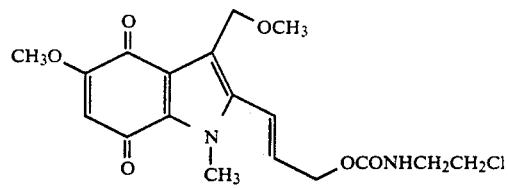

(10) 5-Methoxy-3-methoxymethyl-1-methyl-2-[1H-indole-4,7-dione]prop-β-en-α-yl N-[2-chloro-1-ethyl]carbamate (Compound E.O. 10)

(11) 3-Hydroxymethyl-5-(4-hydroxypiperidino)-1-methyl-2-[1H-indole-4,7-dione]prop-β-en-α-ol (Compound E.O. 11)

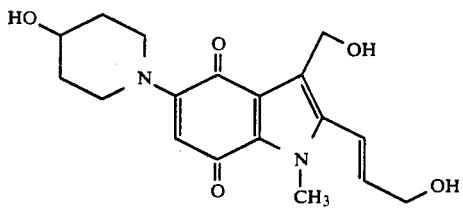

(12) 3-Hydroxymethyl-1-methyl-5-morpholino-2-[1H-indole-4,7-dione]prop-β-en-α-ol (Compound E.O. 12)

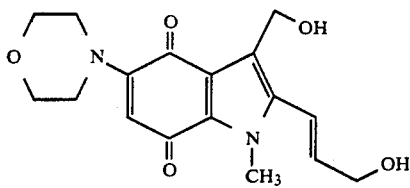

(13) 3-(N-chloroethylcarbamoyloxymethyl)-5-methoxy-1-methyl-2-[1H-indole-4,74,7-dione]prop-β-en-α-yl N-chloroethyl carbamate (Compound E.O. 13)

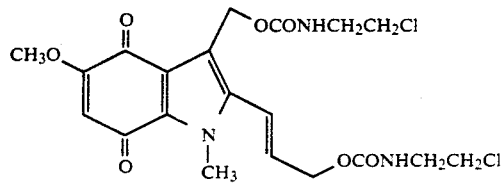

(14) 3-Hydroxymethyl-5-phenylamino-1-methyl-2-[1H-indole-4,7-dione]prop-β-en-α-ol (Compound E.O. 15)

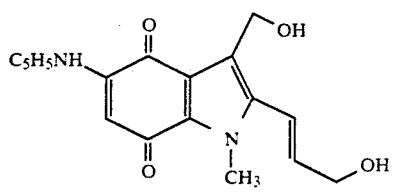

(15) 3-Hydroxymethyl-5-methoxy-1-butyl-2-[1H-indole-4,7-dione]prop-β-en-α-ol (Compound E.O. 16)

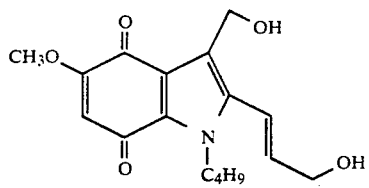

(16) 5-Aziridino-3-hydroxymethyl-1-butyl-2-[1H-indole-4,7-dione]prop-β-en-αol (Compound E.O. 17)

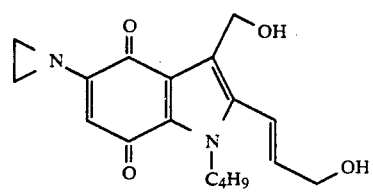

(17) 1,6-Dimethyl-5-hydroxymethyl-5-methoxy-2-[1H-indole-4,7-dione]prop-β-en-α-ol (Compound E.O. 18)

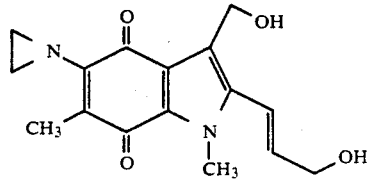

(18) 5-Aziridino-1,6-dimethyl-3-hydroxymethyl-2-[1H-indole-4,7-dione]prop-β-en-α-ol (Compound E.O. 19)

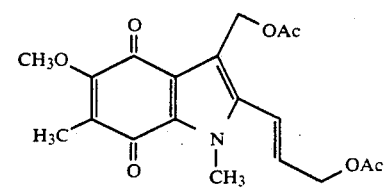

(19) 3-Acetoxymethyl-1,6-dimethyl-5-methoxy-2-[1H-indole-4,7-dione]prop-β-en-α-yl acetate (E.O. 33)

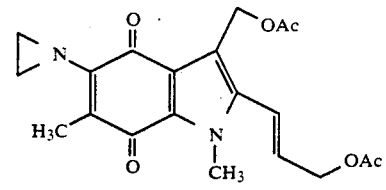

(20) 3-Acetoxymethyl-5-aziridino-1,6-dimethyl-2-[1H-indole-4,7-dione]prop-β-en-αyl acetate (E.O. 35)

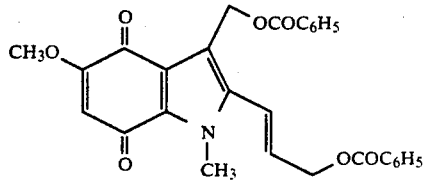

(21) 3-Benzoxymethyl-5-methoxy-1-methyl-2-[1H-indole-4,7-dione]prop-β-en-α-yl benzoate (Compound E.O. 36)

(22) 3-[N-butylcarbamoyloxymethyl]-5-methoxy-1-methyl-2-[1H-indole-4,7-dione]prop-β-en-α-yl N-butylcarbamate (Compound E.O. 37)

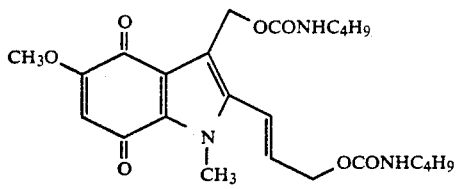

(23) 5-Methoxy-1-methyl-3-[N-phenylcarbamoyloxymethyl]-2-[1H-indole-4,7-dione]prop-β-en-α-yl N-phenylcarbamate (Compound E.O. 38)

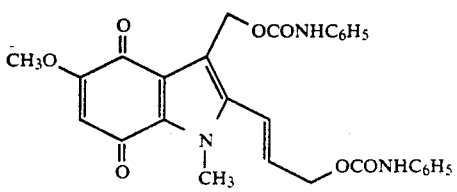

(24) 5-Methoxy-1-methyl-3-(N-phenylaminomethyl)-2-[1H-indole-4,7-dione]prop-β-en-α-yl acetate (Compound E.O. 39)

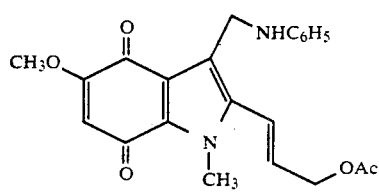

(25) 5-Methoxy-1,3-dimethyl-2-[1H-indole-4,7-dione]-prop-β-en-α-yl acetate (Compound E.O. 41)

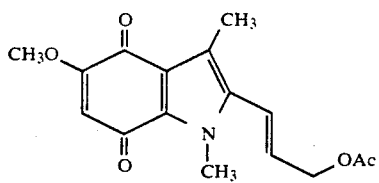

(26) 3-Acetoxymethyl-5-[2-(N,N-dimethylamino)ethyl-1-amino]-1-methyl-2-[1H-indole-4,7-dione]prop-β-en-α-yl acetate (Compound E.O. 47)

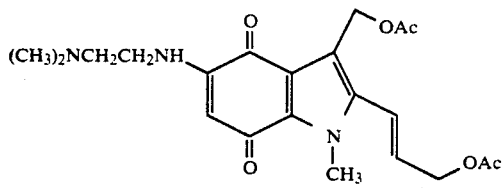

(27) 3-Acetoxymethyl-5-[2-(N,N-dimethylamino)ethyl-1-amino]-1-methyl-2-[1H-indole-4,7-dione]prop-β-en-α-ol (Compound E.O. 48)

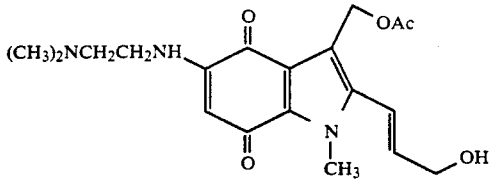

(28) 3-Hydroxymethyl-1-methyl-5-[2-pyridylethyl-1-amino]-2-[1H-indole-4,7-dione]prop-β-en-α-ol (Compound E.O. 51)

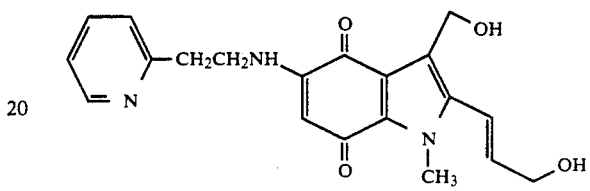

(29) 3-Acetoxymethyl-1-methyl-5-[2-pyridylethyl-1-amino]-2-[1H-indole-4,7-dione]prop-β-en-α-yl acetate (Compound E.O. 52)

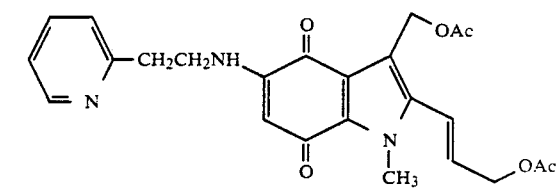

(30) 3-Acetoxymethyl-1-methyl-5-propyleneamino-2-[1H-indole-4,7-dione]prop-β-en-α-yl acetate (Compound E.O. 53)

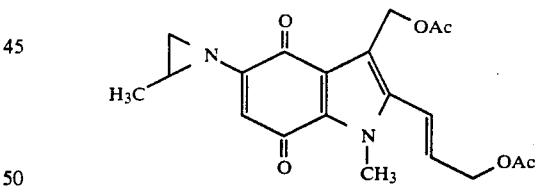

(31) 5-Ethylamino-3-hydroxymethyl-1-methyl-2-[1H-indole-4,7-dione]prop-β-en-α-ol (Compound E.O. 56)

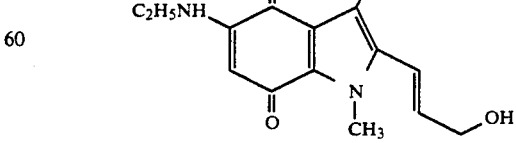

(32) 3-Acetoxymethyl-5-ethylamino-1-methyl-2-[1H-indole-4,7-dione]prop-β-en-α-yl acetate (Compound E.O. 58)

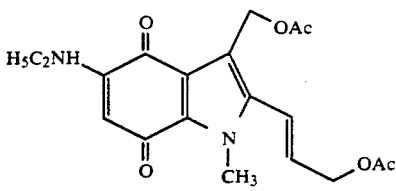

(33) 3-Acetoxymethyl-5-ethylamino-1-methyl-2-[1H-indole-4,7-dione]prop-β-en-α-ol (Compound E.O. 59)

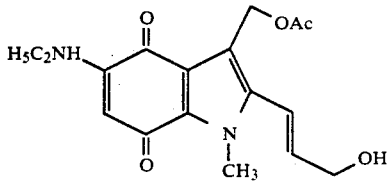

(34) 3-Acetoxymethyl-1-methyl-5-morpholino-2-[1H-indole-4,7-dione]prop-β-en-α-yl acetate (Compound E.O. 60)

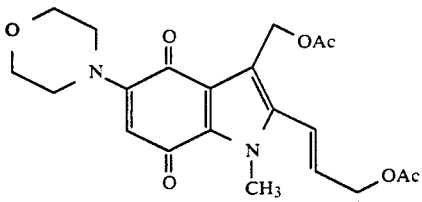

(35) 3-Acetoxymethyl-1-methyl-5-[2-pyridylethyl-1-amino]-2-[1H-indole-4,7-dione]prop-β-en-α-ol (Compound E.O. 62)

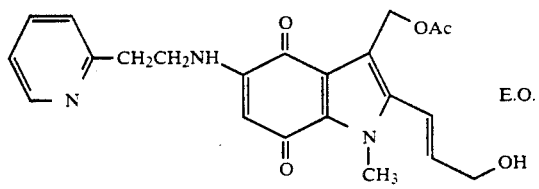

(36) O-ethyl 5-methoxy-1-methyl-2-[1H-indole-4,7-dione]prop-β-en-α-yl dithiocarbamate (Compound E.O. 64)

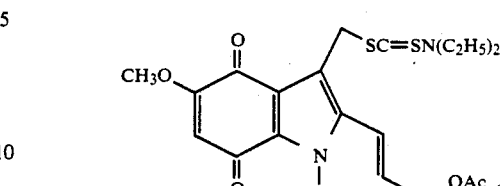

Of the preferred compounds, it has been found that the compounds E.O. 1 to E.O. 6 and E.O. 8 to E.O. 15 can all be prepared from the compound E.O. 7 in simple ways. Thus the compounds E.O. 1 to E.O. 3, E.O. 10 and E.O. 13 can be directly prepared from E.O. 7 by replacing the hydroxy groups $X_1$ and $X_2$ by the required functional groups, which have good "leaving group" properties. The compounds E.O. 8, E.O. 9, E.O. 11 and E.O. 12 can be prepared directly from E.O. 7 by treatment with an excess of the appropriate secondary amine. Finally the compounds E.O. 4, E.O. 5 and E.O. 6 can be prepared by treating the compound E.O. 1 (prepared from E.O. 7 by treatment with acetic anhydride) with an excess of the required primary or seconday amine.

These syntheses, with an indication of the yields obtained for the various compounds, are set out in reaction scheme II, and are illustrated in Examples 2 to 13 below.

The synthesis of compounds E.O. 36 to E.O. 38, E.O. 47, E.O. 48, E.O. 51 to E.O. 53, E.O. 56, E.O. 58, E.O. 59, E.O. 60 and E.O. 62 from either E.O. 1 or E.O. 7 proceeded analogously to the synthesis of the compounds described above. Compounds E.O. 39, E.O. 41 and E.O. 64 have been obtained from indoloquinone E.O. 1 under reductive alkylation conditions, and are illustrated in examples 14 to 16 below.

Indoloquinones E.O. 33 and E.O. 35 have been ultimately obtained from compound E.O. 18.

Selective hydrolysis of one of the acetate groups in the indoloquinones E.O. 1 and E.O. 4 yielded compounds E.O. 1A and E.O. 1B, and E.O. 4A respectively.

SCHEME II

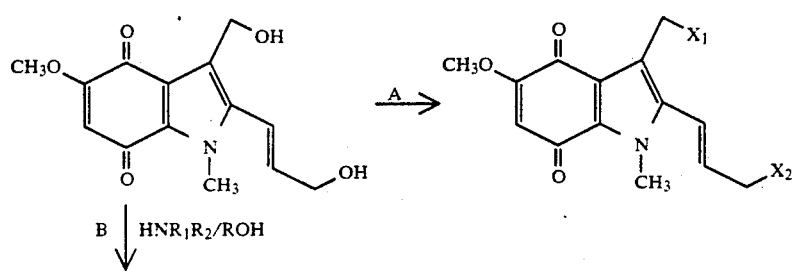

SCHEME II -continued

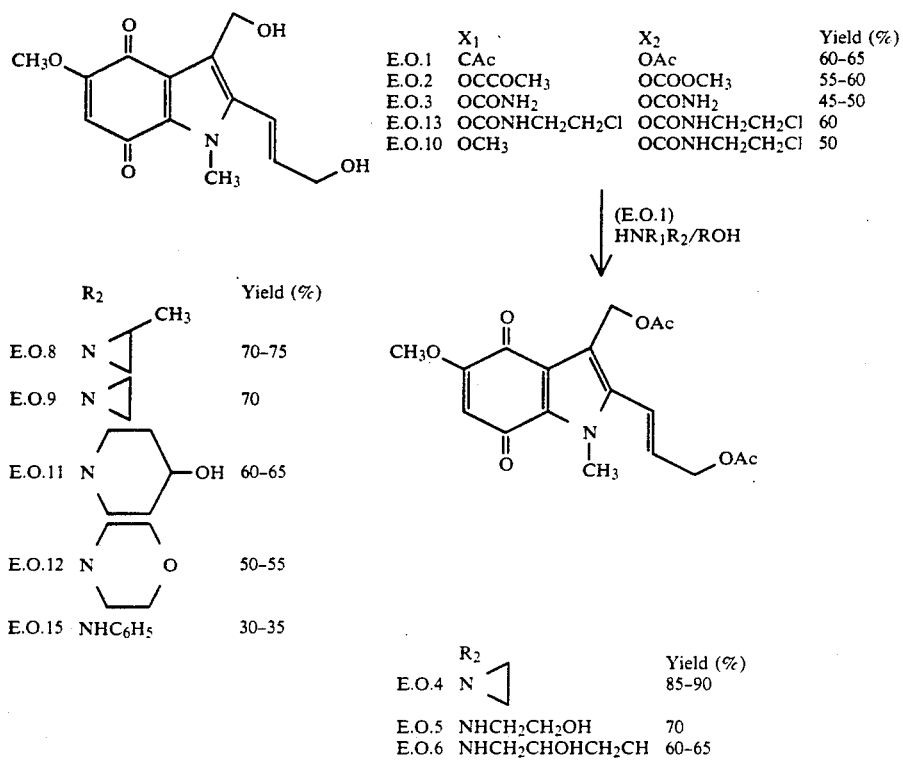

| | X₁ | X₂ | Yield (%) |
|---|---|---|---|
| E.O.1 | CAc | OAc | 60-65 |
| E.O.2 | OCCOCH₃ | OCOOCH₃ | 55-60 |
| E.O.3 | OCONH₂ | OCONH₂ | 45-50 |
| E.O.13 | OCONHCH₂CH₂Cl | OCONHCH₂CH₂Cl | 60 |
| E.O.10 | OCH₃ | OCONHCH₂CH₂Cl | 50 |

| | R₂ | Yield (%) |
|---|---|---|
| E.O.8 | N(CH₃)(CH₂CH₂) | 70-75 |
| E.O.9 | N(azetidine) | 70 |
| E.O.11 | N-piperidine-OH | 60-65 |
| E.O.12 | N-morpholine | 50-55 |
| E.O.15 | NHC₆H₅ | 30-35 |

| | R₂ | Yield (%) |
|---|---|---|
| E.O.4 | N(aziridine) | 85-90 |
| E.O.5 | NHCH₂CH₂OH | 70 |
| E.O.6 | NHCH₂CHOHCH₂CH | 60-65 |

The compound E.O. 7 can itself be prepared starting from m-chlorophenol in accordance with the following reaction scheme:

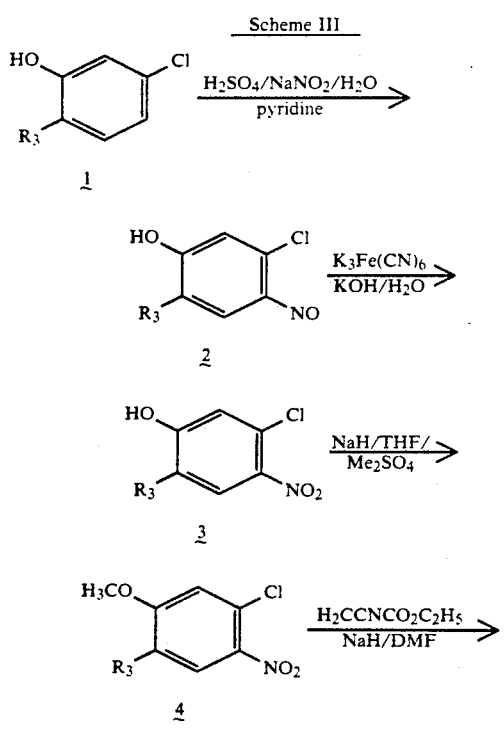

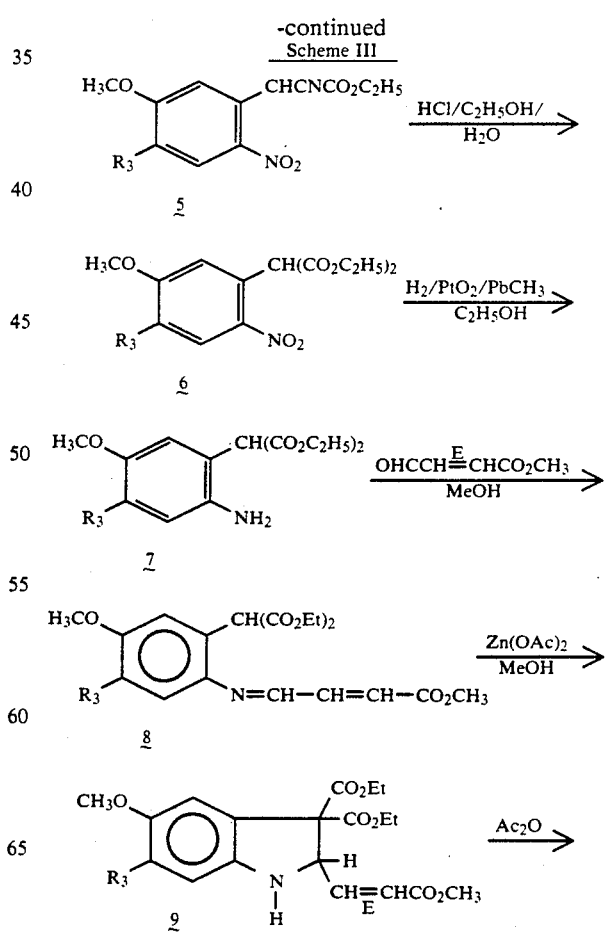

-continued
Scheme III

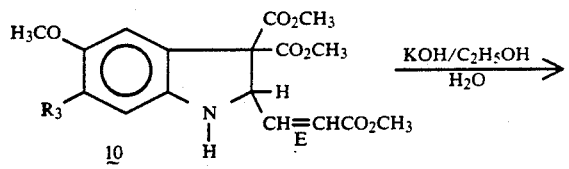

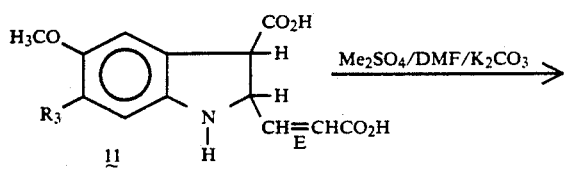

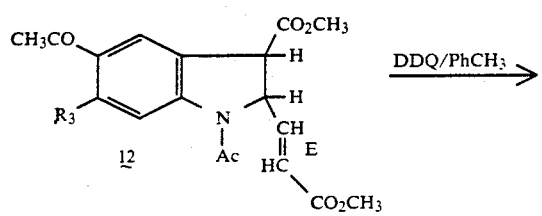

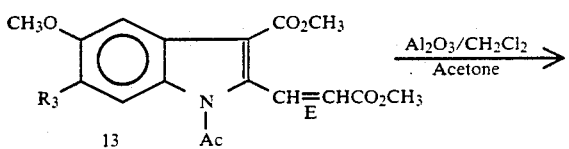

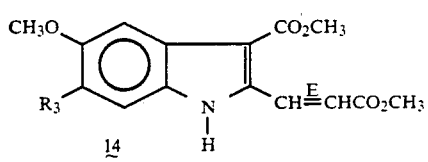

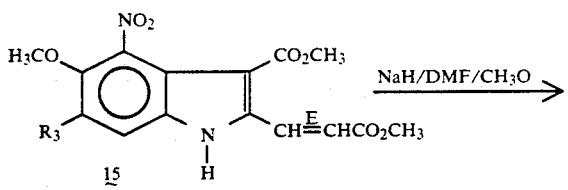

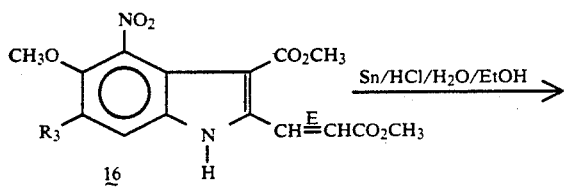

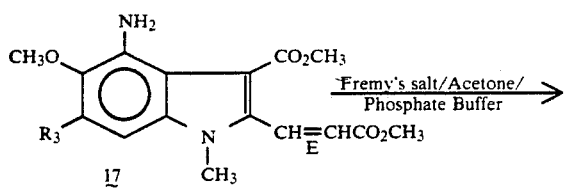

-continued
Scheme III

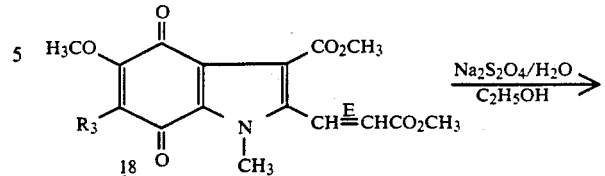

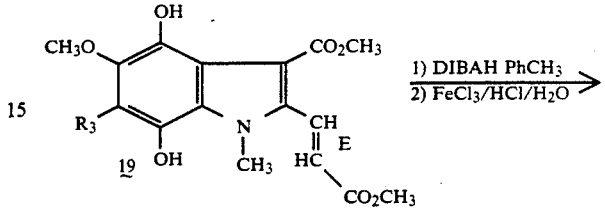

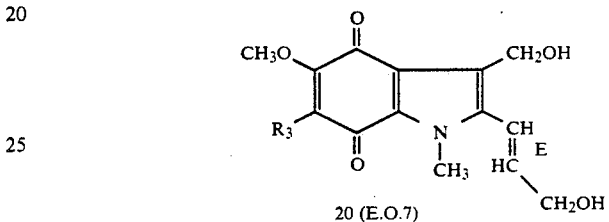

The various steps in the synthesis of compound E.O. 7 in accordance with this reaction are described in detail in the following Example:

EXAMPLE 1

Synthesis of Compound E.O. 7 (20)

3-Chloro-4-nitrophenol (3)

a) Nitrosation of m-chlorophenol (1)

The nitrosation of m-chlorophenol (1) was carried out following the method given by Hodgson et al (J. Chem. Soc. 1940, 1270) for the nitrosation of m-fluorophenol.

A solution of 265.5 g $NaNO_2$ in conc. $H_2SO_4$ (2.54 l) was prepared. The addition of $NaNO_2$ to conc. $H_2SO_4$ took place, while stirring and cooling at +5° C. After the addition of crushed ice (1.2 kg) to this solution at a temperature of +5° C. m-chlorophenol (227.5 g; 1.77 mole) dissolved in pyridine (400 ml) was introduced. Thereupon the reaction mixture was poured into ice water. The crystals were collected by filtration, washed with water and dried in the air.

b) Oxydation of 3-chloro-4-nitrosophenol (2)

The oxydation of 3-chloro-4-nitrosophenol (2) to 3-chloro-4-nitrophenol (3) proceeded as described by Hodgson et al (J. Chem. Soc. 1925, 1579). To a stirred solution of 1.65 kg $K_3Fe(CN)_6$ in 5% KOH aq. (22 l) was added the crude 3-chloro-4-nitrosophenol. Stirring was continued for seven days at room temperature. Thereupon the reaction mixture was acidified dropwise with sulphuric acid and extracted with ether. The ethereal extracts were washed with sat. NaCl aq. and dried with $MgSO_4$. Evaporation of the solvent in vacuo yielded 199.5 g (65%) of crude 3-chloro-4-nitrophenol (solid) which was sufficiently pure for the conversion into 3-chloro-4-nitroanisole.

M.p. 121°-122° C.

3-chloro-4-nitroanisole (4)

In an atmosphere of $N_2$ were added to a stirred suspension of 31 g NaH in 2.2 l anhydrous THF 199.5 g (1.15 mole) 3-chloro-4-nitrophenol (3). This was followed by the addition of dimethylsulfate (575 ml). The whole mixture was heated under reflux during 1.5 h. After cooling, it was poured into a cold (0° C.) diluted $NH_4OH$ solution, to destroy the excess of dimethylsulfate, and stirred for two hours. The product was isolated by extraction with diethylether. The ethereal extracts were dried with $MgSO_4$ and evaporated at reduced pressure affording 156 g (72.4%) of 3-chloro-4-nitroanisole.

$^1H$ NMR $\delta(CDCl_3)$; 8.07 (d, 1H, J=9.5 Hz, H-5), 7.05 (d, 1H, J=2.5 Hz, H-2), 6.99 (d.d, 1H, J=9.5 Hz, J=2.5 Hz, H-6), 3.92 (s, 3H, $OCH_3$).

Ethyl 5-methoxy-2-nitrophenylcyanoacetate (5)

To a suspension of 44.2 g of NaH in DMF (870 ml) was added a solution of ethylcyanoacetate (197.7 g) in anhydrous DMF (162 ml). After the addition the reaction mixture was stirred for 10 minutes. Subsequently 156 g (0.83 mole) 3-chloro-4-nitroanisole were added. The resulting dark solution was heated at 50°–55° C. for 16 h. After cooling, the reaction mixture was poured into cold (0° C.) 5% KOH aq.

The solution thus obtained was washed with ether (3×). Thereupon the solution was acidified with conc. 30% HCl aq., while cooling by adding crushed ice. During the acidification the colour of the mixture turned from dark red to pale yellow. From the collodial solution the product was isolated via an extraction with 1,1,1-trichloroethane (5×). The combined organic layers were dried with $MgSO_4$. After evaporation of the solvent, a red oily residue was obtained, which was employed in the next step without further purification.

Yield: 218.5 g (99.5%: contained only some DMF).

Purification of a sample by flash column chromatography using silicagel and $CH_2Cl_2$ as eluent afforded a pale yellow oil (yield: 95–100%) which crystallized on standing in the refrigerator.

M.p. 44°–47° C. IR($CHCl_3$): 2220 (C≡N), 1740 (ester C=O), 1580 ($NO_2$).

$^1H$ NMR $\delta(CDCl_3)$: 8.28 (d, 1H, J=9 Hz, H-3), 7.27 (d, 1H, J=2.5 Hz, H-6), 7.04 (d.d, 1H, J=2.5 Hz and J=9 Hz, H-4), 5.68 (s, 1H, $CHCNCO_2C_2H_5$), 4.33 (q, 2H, J=7 Hz $CO_2CH_2CH_3$), 3.98 (s, 3H, $OCH_3$), 1.33 (t, 3H, J=7 Hz $CO_2CH_2CH_3$). An exact mass determination gave 264.0759; $C_{12}H_{12}N_2O_5$ requires 264.0772 (4.9).

Diethyl 5-methoxy-2-nitrophenylmalonate (6)

A solution of 85 g (0.32 mole) ethyl 5-methoxy-2-nitrophenylcyanoacetate (5) in a mixture of ethanol (510 ml) and was saturated with HCl gas cooling in ice. The reaction mixture was stirred during two days at room temperature. Thereupon ice water (500 ml) was added and stirring was continued for 24 hrs at room temperature. The crystals, which has been separated were collected by filtration. Recrystallization from aqueous ethanol afforded 85 g (85.4%) of 6 (white crystals).

M.p. 92°–93° C. IR($CHCl_3$): 1725 (ester C=O), 1580 ($NO_2$). $^1H$ NMR $\delta(CDCl_3)$: 8.28 (d, 1H, J=10 Hz, H-3), 6.9–7.05 (m, 2H, H-4 and H-6), 5.44 (s, 1H, $CH$ $CO_2C_2H_5$), 4.30 (q, 4H, J=7 Hz, $CO_2CH_2CH_3$), 3.92 (s, 3H, $OCH_3$), 1.31 (t, 3H, J=7 Hz, $CO_2CH_2CH_3$).

An exact mass determination gave 311.1004; $C_{14}H_{17}NO_7$ requires 311.1004 (0.0).

Methyl 3,3-diethoxycarbonyl-2,3-dihydro-5-methoxy-2-indoleacrylate (9)

a) Catalytic reduction of (6): diethyl 2-amino-5-methoxyphenylmalonate (7)

Diethyl 5-methoxy-2-nitrophenylmalonate (6) (20 g, 64.3 mmol) was reduced with $H_2$ at atmospheric pressure using a mixture of toluene (250 ml) and abs. ethanol (15 ml) as solvent and $PtO_2$ (300 mg) as catalyst. After the theoretical amount of hydrogen was consumed the reaction mixture was filtered through high flow. The filtrate was concentrated in vacuo at a bath temperature beneath 30° C. The resulting pale green oily mixture was, because of its instability, employed in the next step without further purification.

IR($CHCl_3$): 3440 and 3350 (NH), 1730 (ester C=O). $^1H$ NMR $\delta(CDCl_3)$: 6.7–6.9 (m, 3H, aromatic H's), 4.69 (s, 1H, $CHCO_2C_2H_5$), 4.27 (q, 4H, J=7 Hz, $CO_2CH_2CH_3$), 3.77 (s, 3H, $OCH_3$), 3.5–4.0 (br s, 2H, $NH_2$), 1.30 (t, 3H, J=7 Hz, $CO_2CH_2CH_3$).

b) Condensation of diethyl-2-amino-5-methoxyphenylmalonate (7) with methyl 3-formylacrylate The crude diethyl 2-amino-5-methoxyphenylmalonate (7) was dissolved in methanol (350 ml). To this solution was added at room temperature methyl 3-formylacrylate (see, Bohlmann et al, Ber. 89 (1956) 1276) (7.33 g) dissolved in methanol (50 ml). The green reaction mixture was stirred for 15 minutes.

Intermezzo:

For the determination of the spectral properties of the imine 8, the condensation of diethyl 2-amino-5-methoxyphenylmalonate with methyl 3-formylacrylate was carried out using toluene as solvent. After evaporation of the solvent IR and $^1H$ NMR spectra of the residue were recorded.

IR ($CHCl_3$): 1730 (ester C=O). $^1H$ NMR $\delta(CDCl_3)$: 8.23 (d, 1H, J=9 Hz, N=$CH$), 7.47 (dd, 1H, J=16 Hz and J=9 Hz, $CH$=$CHCO_2Me$), 6.7–7.3 (m, 2H, aromatic H's), 6.41 (d, 1H, J=16 Hz, CH=$CHCO_2Me$), 5.51 [s, 1H, $CH(CO_2C_2H_5)_2$], 4.24 (q, 4H, J=7 Hz, $OCH_2CH_3$), 3.84 (s, 3H, $OCH_3$), 1.27 (t, 6H, J=7 Hz, $OCH_2CH_3$).

c) The 1,5-electrocyclisation reaction Cyclisation of the imine 8 to methyl 3,3-diethoxycarbonyl-2,3-dihydro-5-methoxy-2-indoleacrylate (9) was attained by addition of $Zn(OAc)_2$, 2 $H_2O$ (4.5 g) to the methanolic solution of the imine. Stirring was continued for one hour. Thereupon the solvent was removed in vacuo. To the residue were added: 2N HCl (300 ml) and $CH_2Cl_2$ (100 ml). The organic layer was separated and the aqueous phase was extracted with $CH_2Cl_2$. The combined organic layers were washed subsequently with 2N HCl, sat. $NaHCO_3$ aq. and sat. NaCl aq. and dried with $MgSO_4$.

Evaporation of the solvent gave 23.9 g (98.6%) of a reddish oil which was employed in the next step without further purification. Purifying of a sample of the residue by flash column chromatography ($SiO_2$, $CH_2Cl_2$/acetone 95/5) afforded a pale yellow oil.

IR($CHCl_3$): 3375 (NH, w), 1730 (ester C=O). $^1H$ NMR $\delta(CDCl_3)$: 6.6–7.15 (m, 4H, CH=$CHCO_2Me$ and aromatic H's), 6.17 (dd, 1H, J=15.5 Hz and J=1 Hz, CH=$CHCO_2Me$) 5.15 (dd, 1H, J=6.5 Hz and J=1 Hz, N-$CH$), 4-4.5 (m, 4H, $OCH_2$), 3.78 (s, 3H) and 3.73 (s, 3H) (OCH₃ and CO₂CH₃), 3.44 (br s, 1H, N$\underline{\text{H}}$), 1.31 (t, 3H) and 1.20 (t, 3H) (J=7 Hz, OCH₂C$\underline{\text{H}}$₃).

An exact mass determination gave 377.1452; C₁₉H₂₃N₁O₇ requires 377.1430 (5.8).

Methyl N-acetyl-3,3-diethoxycarbonyl-2,3-dihydro-5-methoxy-2-indoleacrylate (10)

The crude indoline 9 was dissolved in acetic anhydride (35 ml). This solution was stirred for 1 h at room temperature. Thereupon the acetic anhydride was removed in vacuo. The residue (~27 g) was sufficiently pure for further conversions. A sample of this residue was purified by flash column chromatography (SiO₂, CH₂Cl₂/acetone 95/5). A pale yellow oily product was obtained.

IR(CHCl₃): 1730 (ester C=O), 1655 (N—C=O). ¹H NMR δ(CDCl₃): 8.07 (br d, 1H, J=7.5 Hz, H-7), 7.13 (d, 1H, J=2.5 Hz, H-4), 6.92 (dd, 1H, J=2.5 Hz, J=7.5 Hz, H-6), 6.75 (dd, 1H, J=15.5 Hz and J=7 Hz, C$\underline{\text{H}}$=CHCO₂Me), 6.03 (dd, 1H, J=15.5 Hz and J=1 Hz, CH=C$\underline{\text{H}}$CO₂Me), 5.68 (br d, 1H, J=7 Hz N—C$\underline{\text{H}}$), 4-4.5 (m, 4H, OC$\underline{\text{H}}$₂CH₃), 3.83 (s, 3H) and 3.72 (s, 3H) (OCH₃ and CO₂CH₃), 2.25 (s, 3H, NCOC$\underline{\text{H}}$₃), 1.30 (s, 3H) and 1.23 (s, 3H) (CO₂CH₂C$\underline{\text{H}}$₃).

N-acetyl-3-carboxy-2,3-dihydro-5-methoxy-2-indoleacrylic acid (11)

The crude N-acetylindole (10) was dissolved in ethanol (270 ml). On cooling in ice a cold (0° C.) solution of KOH (21.6 g) in water (180 ml) was added. Stirring and cooling was continued for 18 h. The reaction mixture was poured into ice water. The resulting solution was extracted with ether (3×) and acidified with 2N HCl. The indoline acid (11) was isolated from the aqueous solution by extraction with CHCl₃ (6×). The combined organic layers were dried over MgSO₄. Evaporation of the volatiles afforded 18.8 g of a foam (96% based on 6).

IR(KBr): 2700–3600 (carboxylic acid OH), 1710 (carboxylic acid C=O). ¹H NMR (acetone-d₆): 8.1 (br s, 1H, H-7), 6.8–7.2 (m, 3H, C$\underline{\text{H}}$=CHCO₂Me, and H-4, H-6), 6.5–7.5 (br s, 2H, carboxylic acid O$\underline{\text{H}}$), 5.95 (d.d, 1H, J=15.5 Hz and J=1.5 Hz, CH=C$\underline{\text{H}}$CO₂Me), 5.6 (br s, 1H, H-2), 4.07 (br s, 1H, H-3), 3.81 (s, 3H, OCH₃), 2.25 (br s, 3H, COC$\underline{\text{H}}$₃).

Methyl N-acetyl-2,3-dihydro-5-methoxy-3-methoxycarbonyl-2-indoleacrylate (12)

To a solution of indoline acid (11) (18.8 g) in anhydrous DMF (250 ml) were added subsequently K₂CO₃ (19.6 g) and dimethylsulfate (52 ml). This mixture was stirred for 4 h at room temperature. Thereupon it was poured into an excess of 2N HCl. The indoline ester derivative (12) was isolated by an extraction with 1,1,1-trichloroethane (4×). The organic extracts were washed with sat. NaCl aq. and dried over MgSO₄. After evaporation of the solvent a reddish oil (~20 g: contained some DMF) was obtained, which could be employed in the next step without further purification. A sample of this residue was purified by flash column chromatography (SiO₂, CH₂Cl₂/acetone 95/5).

IR(CHCl₃): 1730 (ester C=O), 1650 (N—C=O). ¹H NMR δ(CDCl₃): 8.13 (br d, 1H, J=8 Hz, H-7), 6.75–8.05 (m, 3H, H-4, H-6 and C$\underline{\text{H}}$=CHCO₂Me), 5.96 (dd, 1H, J=15.5 Hz, CH=C$\underline{\text{H}}$CO₂Me), 5.45 (br d, 1H, NC$\underline{\text{H}}$), 3.87 (br s, 1H, C$\underline{\text{H}}$CO₂C₂H₅), 3.81 (s, 3H), 3.77 (s, 3H) and 3.73 (s, 3H) (OC$\underline{\text{H}}$₃ and CO₂C$\underline{\text{H}}$₃), 2.24 (s, 3H, NCOC$\underline{\text{H}}$₃).

An exact mass determination gave 333.1240; C₁₇H₁₉N₁O₆ requires 333.1212 (8.4).

Methyl 5-methoxy-3-methoxycarbonyl-2-indoleacrylate (14)

A solution of the crude indoline (12) in toluene was heated under reflux with 1.05 eq. of DDQ for 18 h. A greyish precipitate of DDQ H₂ was formed, which was removed by filtration. Thereupon the toluene was evaporated in vacuo. A very dark coloured residue containing methyl N-acetyl-5-methoxy-3-methoxycarbonyl-2-indoleacrylate (13) was obtained.

Intermezzo:

A sample of this residue was submitted to flash column chromatography (SiO₂, CH₂Cl₂/acetone 95/5) affording a reddish oil which has been characterized by IR, ¹H NMR and mass spectrometry.

IR(CHCl₃): 1710 (ester C=O). ¹H NMR δ(CDCl₃): 8.25 (d, 1H, J=16 Hz, C$\underline{\text{H}}$=CHCO₂Me), 7.94 (d, 1H, J=9 Hz, H-7), 7.60 (d, 1H, J=2.5 Hz, H-4), 7.02 (dd, J=9 Hz and J=2.5 Hz, H-6), 6.22 (d, 1H, J=16 Hz, CH=C$\underline{\text{H}}$CO₂Me), 4.98 (s, 3H), 4.91 (s, 3H) and 4.87 (s, 3H) (OC$\underline{\text{H}}$₃ and CO₂CH₃), 2.60 (s, 3H, NCOCH₃).

An exact mass determination gave 331.1056; C₁₇H₁₇N₁O₆ requires 333.1056 (0.0).

Purifying this residue via column chromatography using Al₂O₃ (basic) and mixtures of CH₂Cl₂ and acetone (8/2→5/5) as eluents afforded 11.07 g of the N-deacetylated indole derivative (13) as yellow crystals (59% based on 6). M.p. 206°–207° C. (MeOH). IR(KBr): 3290 (NH, vs), 1690 (ester C=O).

¹H NMR δ(DMSO-d₆): 12.32 (br s, 1H, NH), 8.44 (d, 1H, J=16 Hz, C$\underline{\text{H}}$=CHCO₂Me), 7.51 (d, 1H, J=2.5 Hz H-4), 7.42 (d, 1H, J=8.5 Hz, H-7), 6.99 (dd, 1H, J=8.5 Hz and J=2.5, H-6), 6.78 (d, 1H, J=16 Hz, CH=C$\underline{\text{H}}$CO₂Me), 3.93 (s, 3H), 3.84 (s, 3H) and 3.81 (s, 3H) (CO₂Me and OCH₃).

An exact mass determination gave 289.0950; C₁₅H₁₅N₁O₅ requires 289.0950 (0.0).

Methyl 5-methoxy-3-methoxycarbonyl-4-nitro-2-indoleacrylate (15)

To a solution of 9.2 g (31.8 mmol) of methyl 5-methoxy-3-methoxycarbonyl-2-indoleacrylate (14) in acetic acid (123 ml), cooled in an ice/water bath, a cold (0° C.) mixture of fuming nitric acid (16.5 ml) and acetic acid (64 ml) was added. The whole mixture was stirred subsequently for 2.5 h at room temperature. A yellow suspension was obtained, which was poured into ice/water. The crystals were collected by filtration washed with water and dried at 50°–60° C. in vacuo.

Yield: 9.34 g (88%). M.p. 243°–245° C. (MeOH).

IR(KBr): 3290 (indole NH), 1700 (ester C=O).

¹H NMR δ(DMSO-d₆): 12.88 (br s, 1H, NH), 8.21 (d, 1H, J=16.4 Hz, C$\underline{\text{H}}$=CHCO₂Me), 7.70 (d, 1H, J=9.1 Hz, Ar H), 7.39 (d, 1H, J=9.1 Hz, Ar H), 6.06 (d, 1H, J=16.4 Hz, CH=C$\underline{\text{H}}$CO₂Me), 3.93 (s, 3H), 3.79 (s, 3H), 3.73 (s, 3H).

An exact mass determination gave 334.0805; C₁₅H₁₄N₂O₇ requires 334.0801 (1.2).

Methyl 5-methoxy-3-methoxycarbonyl-N-methyl-4-nitro-2-indoleacrylate (16)

This synthesis was carried out under an atmosphere of dry $N_2$. To a stirred suspension of NaH (2.9 g) in dimethylformamide (145 ml) were added 9.34 g (28 mmol) methyl 5-methoxy-3-methoxycarbonyl-4-nitro-2-indoleacrylate (15). Thereupon the whole mixture was heated at 45°–50° C. When the evolution of $H_2$ had ceased methyliodide (25 ml) was added to the dark red solution. During an additional (1 h) heating of the reaction mixture at 60° C., the colour of the solution turned to yellow. After cooling this mixture was poured into cold (0° C.) 10% $NaHSO_4$ aq. Yellow crystals separated, which were collected by filtration, washed with water and ethanol, and finally dried in vacuo at 50°–60° C.

Yield: 9.23 g (95%). M.p. 211°–213° C.

IR(KBr): 1700 (ester C=O).

$^1H$ NMR $\delta$(DMSO-$d_6$), 8.06 (d, 1H, J=16.5 Hz CH=CHCO$_2$Me), 7.96 (d, 1H, J=9 Hz, aromatic H), 7.43 (d, 1H, J=9 Hz, aromatic H), 6.68 (d, 1H, J=16.5 Hz CH=CHCO$_2$Me), 3.93 (s, 6H), 3.83 (s, 3H) and 3.71 (s, 3H).

An exact mass determination gave 348.0946; $C_{16}H_{16}N_2O_7$ requires 348.0957 (3.2).

Methyl 4-amino-5-methoxy-3-methoxycarbonyl-N-methyl-2-indoleacrylate (17)

To a suspension of 9.23 g (26.5 mmol) methyl 5-methoxy-3-methoxycarbonyl-N-methyl-4-nitro-2-indoleacrylate (16) in ethanol (745 ml) were added subsequently tin (14.9 g) and 3N HCl (200 ml). This mixture was heated under reflux for 30 minutes. Thereupon the solution was decanted from the excess of tin and neutralized with sat. aq. $NaHCO_3$. The red suspension thus obtained was added to an equal volume of water. The aqueous phase was extracted with $CHCl_3$(5×). The combined organic layers were washed with sat. aq. NaCl aq. (2×), dried over $MgSO_4$ and concentrated at reduced pressure. A red crystalline (7.94 g) residue was obtained which could be employed in the next reaction step without further purification.

M.p. 164.5°–165.5° C. (MeOH, red crystals).

IR(KBr): 3470 and 3350 ($NH_2$), 1710 (ester C=O).

$^1H$ NMR $\delta$(DMSO-$d_6$): 8.08 (d, 1H, J=16.5 Hz, CH=CHCO$_2$Me), 7.05 (d, 1H, J=8.8 Hz, Ar H), 6.75 (d, 1H, J=8.8 Hz, Ar H), 6.44 (d, 1H, J=16.5 Hz, CH=CHCO$_2$Me), 5.83 (br s, 2H, $NH_2$), 3.85 (s, 3H), 3.81 (s, 3H), 3.80 (s, 3H), 3.77 (s, 3H). An exact mass determination gave 318.1227; $C_{16}H_{18}N_2O_5$ requires 318.1216 (3.5).

Methyl 5-methoxy-3-methoxycarbonyl-N-methyl-4,7-dioxo-2-indoleacrylate (18)

To a solution of 7.95 g (25 mmol) methyl 4-amino-5-methoxy-3-methoxycarbonyl-N-methyl-2-indoleacrylate (17) in acetone (1.0 l) was added a solution of Fremy's salt (33.65 g) in a $NaH_2PO_4$/$Na_2HPO_4$ buffer (1.0 l, 0.3M; pH 6). The whole mixture was stirred at room temperature for 1 h. The orange-brown crystals, which had been separated, were collected by filtration, washed with water and methanol, and dried in vacuo at 50°–60° C., affording 5.75 g of indoloquinone (18). To obtain a second crop the filtrate was extracted with $CH_2Cl_2$ (4×). The combined organic layers were washed subsequently with sat. NaCl aq. and dried with $MgSO_4$. After evaporation of the solvents a dark red residue was obtained, from which by flash column chromatography (SiO$_2$, $CH_2Cl_2$/acetone 95/5) a second crop of 1.1 g of indoloquinone (18) could be isolated.

Total yield: 6.85 g (82%). M.p. 235°–236° C.

IR(KBr): 1715 (ester C=O), 1680 (quinone C=O), 1600 (quinone C=O).

$^1H$ NMR $\delta$(DMSO-$d_6$): 7.63 (d, 1H, J=16.5 Hz, CH=CHCO$_2$Me), 6.38 (d, 1H, J=16.5 Hz, CH=CHCO$_2$Me), 5.96 (s, 1H, H-6), 4.05 (s, 3H), 3.84 (s, 3H), 3.81 (s, 3H) and 3.76 (s, 3H).

An exact mass determination gave 333.0843; $C_{16}H_{15}N_1O_7$ requires 333.0838 (1.5).

Methyl 4,7-dihydroxy-5-methoxy-3-methoxycarbonyl-N-methyl-2-indoleacrylate (19)

Methyl 5-methoxy-3-methoxycarbonyl-N-methyl-4,7-dioxo-2-indoleacrylate (18) (6.64 g, 20 mmol) was dissolved in a mixture of chloroform (600 ml) and ethanol (215 ml). The reduction was carried out on stirring with an aqueous solution (260 ml) of $Na_2S_2O_4$ (42 g) at room temperature for 30 minutes.

The organic layer was separated and washed with sat. NaCl aq., dried over $MgSO_4$ and concentrated under reduced pressure. The residue (6.6 g; 99%) was sufficiently pure for the employment in the next reaction step.

IR(KBr): 3200–3500 (OH), 1720 (ester C=O).

$^1H$ NMR $\delta$(DMSO-$d_6$): 10.60 (s, 1H, OH), 9.48 (br s, 1H, OH), 8.04 (d, 1H, J=16.5 Hz, CH=CHCO$_2$Me), 6.53 (s, 1H, H-6), 6.44 (d, 1H, J=16.5 Hz, CH=CHCO$_2$Me), 4.06 (s, 3H), 3.90 (s, 3H), 3.83 (s, 3H) and 3.76 (s, 3H).

3-Hydroxymethyl-5-methoxy-1-methyl-2-[1H-indole-4,7-dione]prop-$\beta$-en-$\alpha$-ol (20 or E.O. 7)

To a stirred suspension of 6.6 g (19.7 mmol) of methyl 4,7-dihydroxy-5-methoxy-3-methoxycarbonyl-N-methyl-2-indoleacrylate (19) in anhydrous $CH_2Cl_2$ (700 ml) was added under an atmosphere of dry $N_2$ a 1.5M solution of diisobutylaluminiumhydride (DIBAL-H) in toluene (119 ml) keeping the temperature below $-30°$ C. The whole mixture was stirred for 2.5 h at 0° C. Thereupon 198 ml 1N (0.1N HCl) FeCl$_3$ were added, keeping the temperature at 0° C. on cooling in a Dry-Ice/ethanol bath. The reaction mixture was stirred for 10 min at 0° C. and filtered subsequently through high flow. The dark red upper layer of the filter cake was extracted with hot $CHCl_3$ (6×). The organic layer of the filtrate and the combined $CHCl_3$ extracts were washed with sat. NaCl aq. (2×) and dried over $MgSO_4$. Evaporation of the volatiles gave 4.4 g of a dark crystalline residue. Flash column chromatography (SiO$_2$, $CH_2Cl_2$/acetone 7/3) afforded 3.0 g (55%) of E.O. 7 (purple crystals).

M.p. 216°–218° C. ($CH_2Cl_2$/acetone 6/4).

IR(KBr): 3100–3600 (OH), 1680 (quinone C=O), 1600 (quinone C=C).

$^1H$ NMR $\delta$(CDCl$_3$): 6.48 (d, 1H, J=16.1 Hz, CH=CHCH$_2$OH), 6.14 (dt, 1H, J=16.1 Hz and J=6.4 Hz, CH=CH$_2$OH), 5.66 (s, 1H, H-6), 4.68 (d, 2H, J=6.4 Hz, CH=CHCH$_2$OH), 4.38 (s, 2H, Ar—CH$_2$OH), ~3.9 (br s, 1H, OH), 3.91 (s, 3H), 3.82 (s, 3H).

An exact mass determination gave 277.0950; $C_{14}H_{15}NO_5$ requires 277.0950 (0.0).

NOTES

IR spectra were recorded on a Perkin-Elmer 257 instrument. $^1$H NMR spectra were taken on Varian A-10 and Brucker WM 250 instruments. Chemical shifts are reported as δ values in ppm relative to TMS (δTMS=0.0 ppm). All mass spectral data were recorded on an AEI-902 or Varian Mat 711 mass spectrometer. Figures in the parentheses after exact mass determinations give the absolute value between calculated and recorded masses (in ppm). Melting points are uncorrected.

The new bioreductive alkylating indoloquinones of the present invention are believed to act as cytostatic agents to interfere with DNA replication (Scheme IV). Reduction of the benzoquinone ring and consecutive elimination of both leaving groups X leads to a very reactive bisvinylogous ortho-quinon methide (D). On anchoring, via a Michael addition, both complementary strands of DNA to this compound, crosslinking occurs, resulting in disturbance of the DNA-replication process.

The reductive alkylation mechanism of the indoloquinones (II) has been studied in more detail. For this purpose a number of these compounds have been subjected to various reduction conditions (Scheme V). Upon treatment of para-indoloquinone derivative 21 ($R_2$=OCH$_3$) with $Na_2S_2O_4$ in the presence of a weak external nucleophile [(a para substituted derivative of) aminobenzene] the C-10 adducts (22) were obtained, the acyl substituent at C-1" carbon atom still being present.

Scheme IV

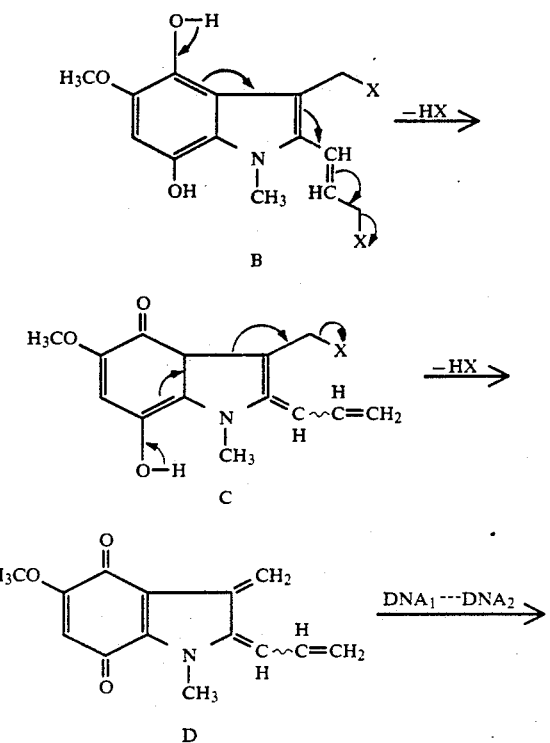

Most significantly, if the reaction was run in the absence of the weak nucleophile but in the presence of Et$_3$N the product appeared to be the 3-methyl derivative 23.

Scheme V

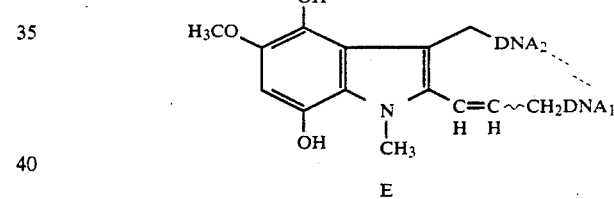

$R_2$ = OCH$_3$
$R_2$ = NHC$_2$H$_5$

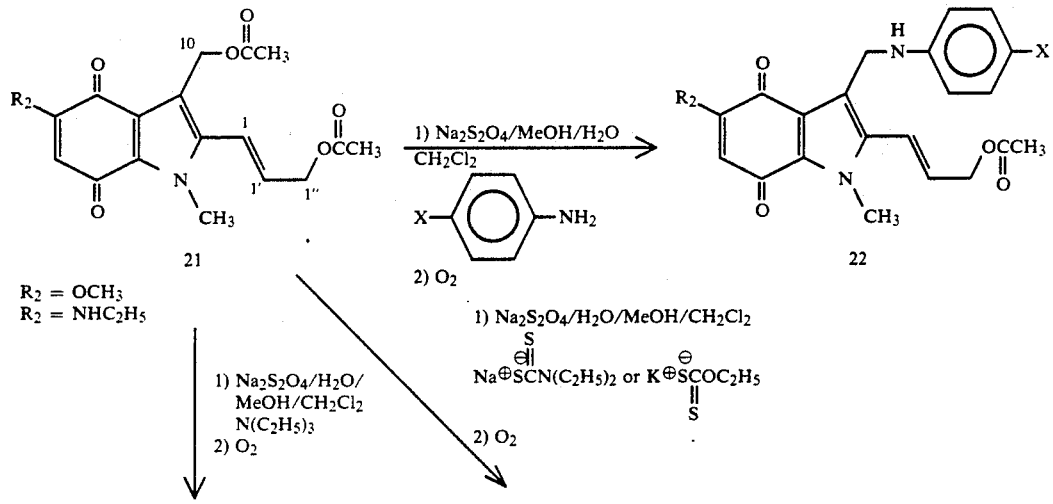

-continued
Scheme V

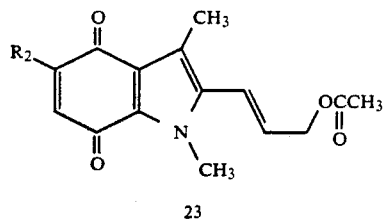

23

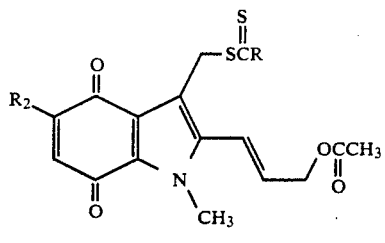

24

R = N(C$_2$H$_5$)$_2$
R = OC$_2$H$_5$

The formation of C-10 adducts has also been observed on trapping the reactive intermediates, obtained after Na$_2$S$_2$O$_4$ reduction of indoloquinones 21 (R$_2$=OCH$_3$ or NHC$_2$H$_5$), with sulphur nucleophiles: potassium ethylxanthate or sodium N,N-diethyl-dithiocarbamate anions. Most understandingly these reactions do not proceed in the absence of Na$_2$S$_2$O$_4$.

Scheme VI

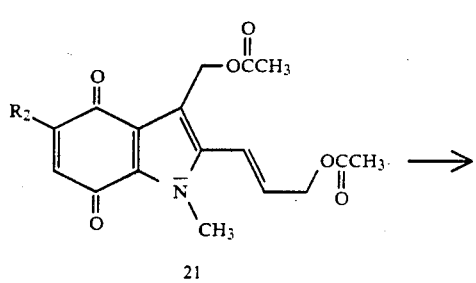

21

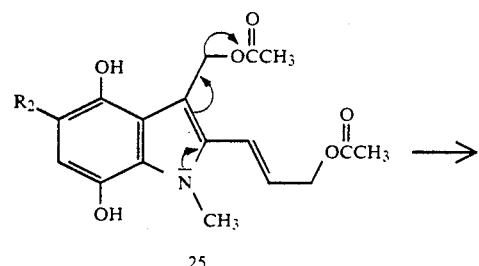

25

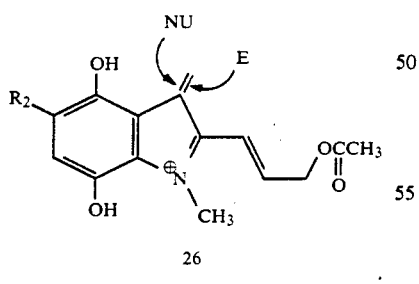

26 a. R$_2$ = OCH$_3$
b. R$_2$ = NHC$_2$H$_5$

From these results we can conclude that the bioreductive alkylating indoloquinones 21 are exclusively activated at the C-10 carbon atom upon Na$_2$S$_2$O$_4$ reduction. This in contrast to the activation process observed with the mitomycins, which yielded for the greater part C-1 adducts. The mechanism of activation of the C-10 carbon atoms has been depicted in Scheme VI. The reactive intermediate 26 can undergo nucleophilic as well as electrophilic addition reactions.

In addition to the formation of reactive iminium species reduction experiments with H$_2$/PtO$_2$ have provided evidence for the intermediacy of quinone methides (27, 28), on trapping them with electrophiles (H$^+$ or D$^+$), and indolodihydroquinone (29) Under suitable chosen conditions the quinone methides might also undergo nucleophilic addition reactions [Scheme VII; see E. A. Oostveen and W. N. Speckamp, Mitomycin analogs I. Indoloquinones as (potential) bisalkylating agents, Tetrahedron, 43; 255-262 (1987)].

Scheme VII

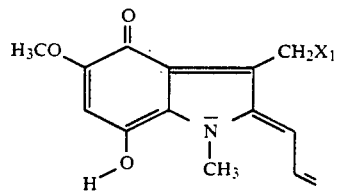

27

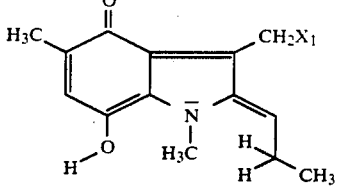

28

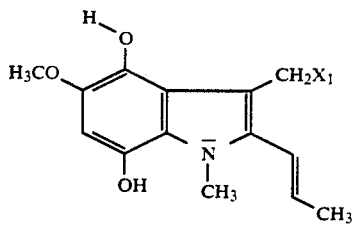

29

The influence of the R$_2$-quinone substituent has been clearly demonstrated upon carrying out the reduction (H$_2$/PtO$_2$) of indoloquinones 30a and 30b (Scheme VIII). The elimination of the OAc-group is stimulated by an electron donating substituent, which is in agreement with the (bio)reductive activation mechanism.

Scheme VIII

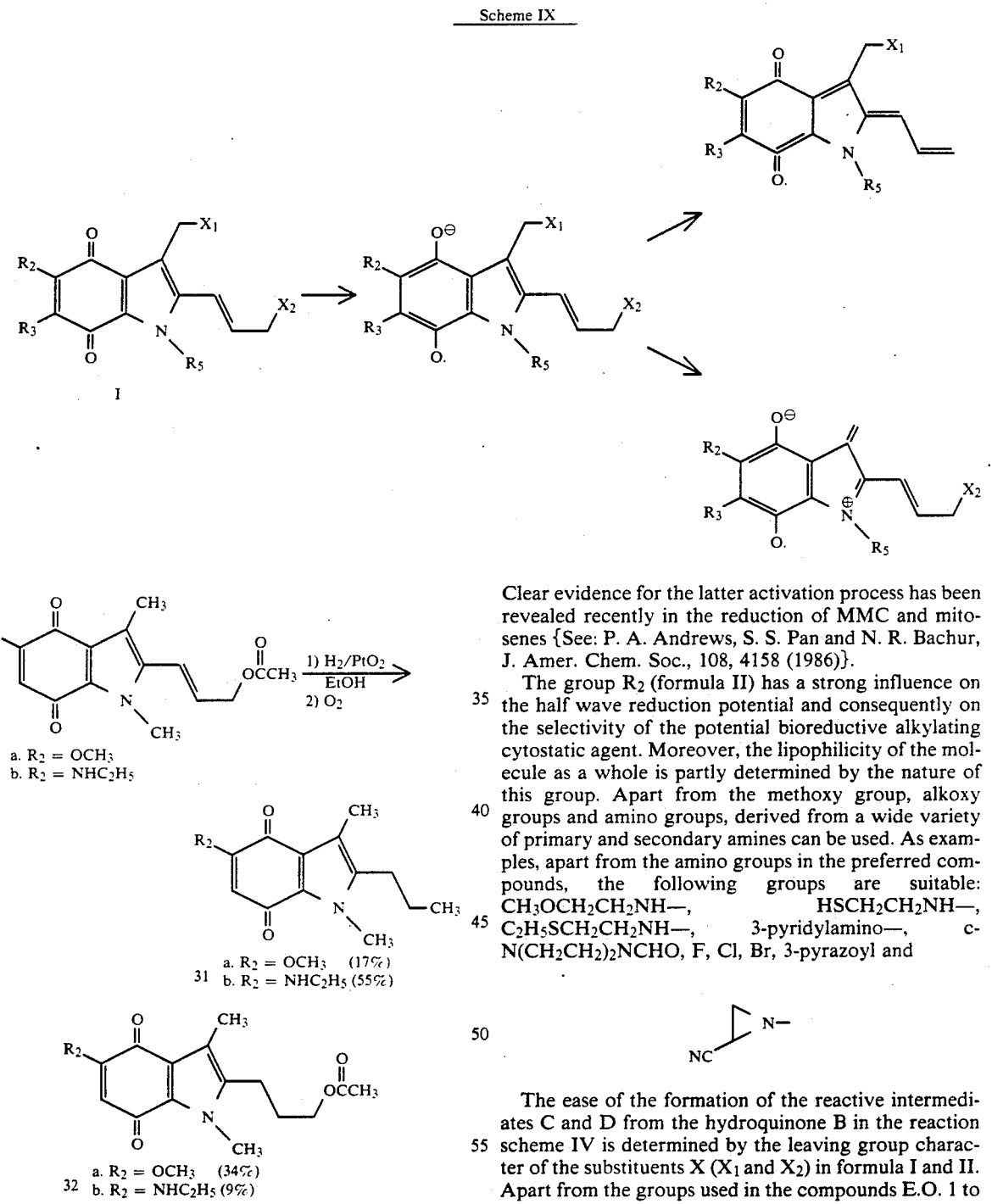

Scheme IX none radical anions—decompose to alkylating intermediates (Scheme IX).

30 a. $R_2 = OCH_3$
b. $R_2 = NHC_2H_5$ 31 a. $R_2 = OCH_3$ (17%)
b. $R_2 = NHC_2H_5$ (55%)

32 a. $R_2 = OCH_3$ (34%)
b. $R_2 = NHC_2H_5$ (9%)

During the activation sequence the NHEt group may also function as an internal proton acceptor. It has also been observed that this role can also be exerted by an external base ($Et_3N$; See last reference mentioned above).

So far it has been assumed that for the formation of the quinone methides and the iminium compounds from indoloquinones (II) a 2 electron/$2H^+$ reduction sequence is required. It is also possible, however, that one-electron reduced indoloquinones (II)—semiquinone radical anions—decompose to alkylating intermediates (Scheme IX).

Clear evidence for the latter activation process has been revealed recently in the reduction of MMC and mitosenes {See: P. A. Andrews, S. S. Pan and N. R. Bachur, J. Amer. Chem. Soc., 108, 4158 (1986)}.

The group $R_2$ (formula II) has a strong influence on the half wave reduction potential and consequently on the selectivity of the potential bioreductive alkylating cytostatic agent. Moreover, the lipophilicity of the molecule as a whole is partly determined by the nature of this group. Apart from the methoxy group, alkoxy groups and amino groups, derived from a wide variety of primary and secondary amines can be used. As examples, apart from the amino groups in the preferred compounds, the following groups are suitable: $CH_3OCH_2CH_2NH—$, $HSCH_2CH_2NH—$, $C_2H_5SCH_2CH_2NH—$, 3-pyridylamino—, c-$N(CH_2CH_2)_2NCHO$, F, Cl, Br, 3-pyrazoyl and

The ease of the formation of the reactive intermediates C and D from the hydroquinone B in the reaction scheme IV is determined by the leaving group character of the substituents X ($X_1$ and $X_2$) in formula I and II. Apart from the groups used in the compounds E.O. 1 to E.O. 64, the groups $—OCONHCH_3$, $—OSO_2CH_3$, $—O$-$SOCH_3$, $—NHAr$, $—SC\!=\!SN(Et)_2$, and $—OSO_2C_6$-$H_{5-p-CH_3}$, may be particularly mentioned.

By following reaction scheme III, using an appropriately alkyl-substituted alkylbenzene to prepare the compound I, indoloquinones in which $R_3$ is an alkyl group can readily be obtained. In this way, the compound E.O. 18 can be prepared, in which $R_2\!=\!OCH_3$; $R_3\!=\!CH_3$ and $X_1\!=\!X_2\!=\!OH$. This compound can be easily converted into the corresponding 5-aziridino compound E.O. 19.

Where the group $R_2$ is —O-alkyl, various alkyl groups can be introduced using 2-alkyl-5-chloro-4-nitrophenol as substrate.

Substituents $R_2$ different from —O-alkyl and/or $R_3$ different from H, alkyl, can be introduced in the reaction scheme III by using suitably substituted o-chloronitrobenzenes.

The N-substituent $R_5$ (Formula I) can be an alkyl group other than methyl and this can be effected using the reaction scheme III by treating the indole derivative 15 with $R_5X$ (where X=halogen and $R_5$=the required alkyl group) in the presence of a suitable base. In this way, the lipophylicity of the molecule as a whole can be varied without considerably affecting the reduction potential. As an example, in order to enhance the lipophylicity of the compounds E.O. 7 and E.O. 9, the compound E.O. 16 in which the N—$CH_3$ grouping of E.O. 7 has been replaced by N—$C_4H_9$, has been prepared in this way and from this compound E.O. 17 which corresponds to the compound E.O. 9 except that the N-substituent ($R_5$) is $C_4H_9$, has been prepared in an analogous way to the preparation of E.O. 9 from E.O. 7.

So far as alkyl group substituents $R_6$, $R_7$, $R_{11}$ and $R_{12}$ are concerned, these can be introduced in the reaction scheme III in either of the two ways:

(a) before the electrocyclization reaction, by choosing appropriate aldehydes for the condensation reaction with the aniline derivative 7; or (b) by the introduction of the required $R_6$ to $R_9$ groups after the 1,5-electrocyclization into the —CH=$CHCO_2CH_3$ substituent group (or other Z substituent group) by means of a suitable reaction sequence.

Bioreductive alkylation is possibly, besides redox cycling, one of the underlying mechanisms of cytotoxicity of the compounds of formula (I), in which the groups $R_8$ and $R_9$ are —$CO_2R_{10}$ and —$CO_2R_{13}$ respectively, or a group $CO_2^-M^+$ ($M^+$ being a metal ion).

This has been established by catalytic reduction ($H_2/PtO_2$) of indoloquinones E.O. 14 and E.O. 57 in EtOD (Scheme X). The cytotoxic intermediate quinone methides (34) have been trapped by deuterium ions.

Scheme X

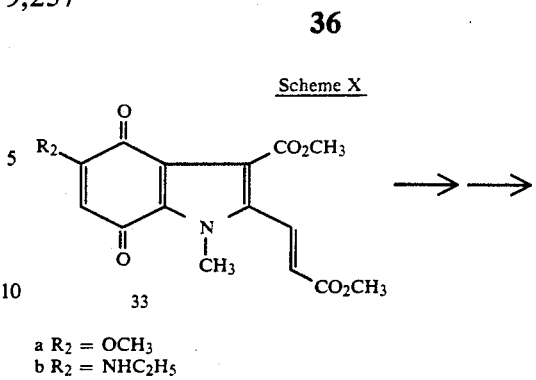

a $R_2$ = $OCH_3$
b $R_2$ = $NHC_2H_5$

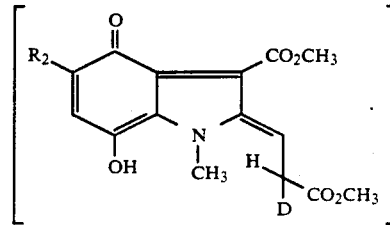

34

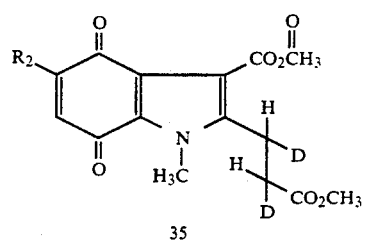

35 a R = $OCH_3$ : 50% D-incorperation
b R = $NHC_2H_5$ : 75% D-incorperation

The high cytotoxic activities of indoloquinone E.O. 22 has to be ascribed to the presence of a second (bioreductive)alkylation center. Bioreductive alkylation experiments using N,N-diethyldithiocarbamate anions as nucleophiles have provided evidence for this additional alkylation center (Scheme XI).

Scheme XI

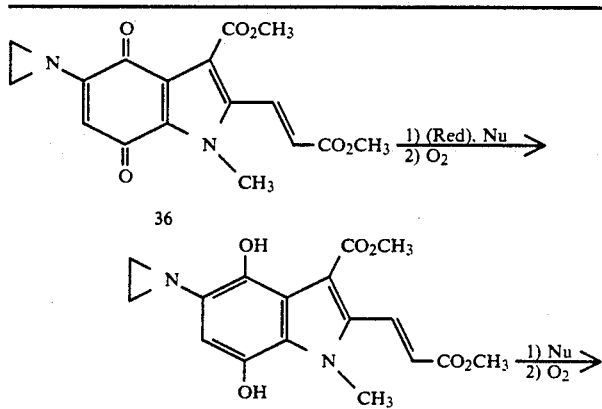

Scheme XI-continued

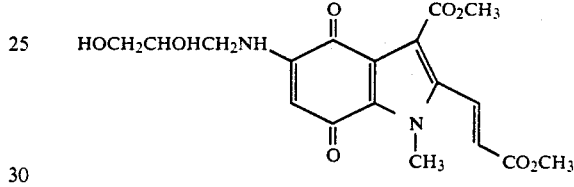

|  | time | conversion (%) |
|---|---|---|
| A $Na^{\oplus}\overset{\ominus}{\underset{\parallel}{S}}CN(C_2H_5)_2/CH_2Cl_2/MeOH/H_2O$: | 24 hr | 20% |
| B $Na^{\oplus}\overset{\ominus}{\underset{\parallel}{S}}CN(C_2H_5)_2/CH_2Cl_2/MeOH/H_2O/Na_2S_2O_4$: | 20 min | 89% |

Preferred compounds of this type, which have been found to have cytostatic activies are the compounds of the general formula:

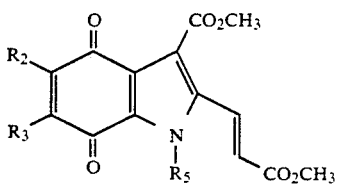

(III)

where $R_2$, $R_3$ and $R_5$ are as in general formula I.

Particularly preferred indoloquinone compounds with the general formula III are:

(37) Methyl 5-methoxy-3-methoxycarbonyl-1-methyl-2-[1H-indole-4,7-dione]acrylate (Compound E.O. 14)

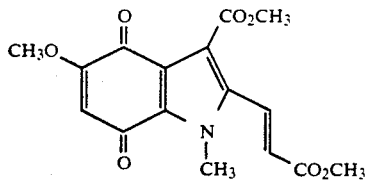

(38) Methyl 5-aziridino-3-methoxycarbonyl-1-methyl-2-[1H-indole-4,7-dione]acrylate (Compound E.O. 22)

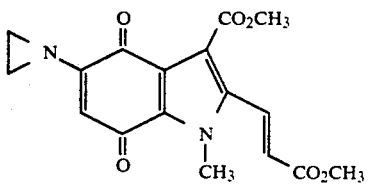

(39) Methyl 5-(2,3-dihydroxypropyl-1-amino)-3-methoxycarbonyl-1-methyl-2-[1H-indole-4,7-dione]acrylate (Compound E.O. 23)

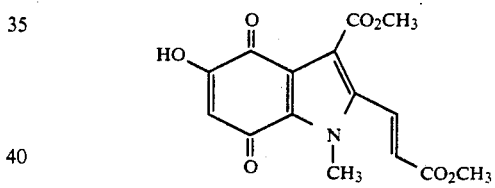

(40) Methyl 5-hydroxy-3-methoxycarbonyl-1-methyl-2-[1H-indole-4,7-dione]acrylate (Compound E.O. 24)

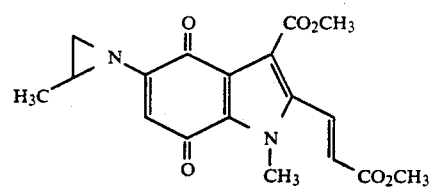

(41) Methyl 3-methoxycarbonyl-1-methyl-5-propyleneamino-2-[1H-indole-4,7-dione]acrylate (Compound E.O. 28)

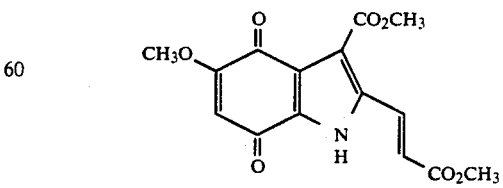

(42) Methyl 5-methoxy-3-methoxycarbonyl-2-[1H-indole-4,7-dione]acrylate (Compound E.O. 29)

(43) Methyl 1,6-dimethyl-5-methoxy-3-methoxycarbonyl-2-[1H-indole-4,7-dione]acrylate (Compound E.O. 32)

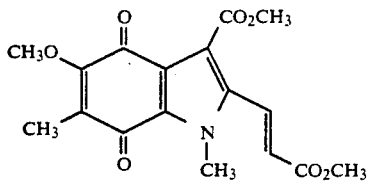

(44) Methyl 5-aziridino-1,6-dimethyl-3-methoxycarbonyl-2-[1H-indole-4,7-dione]acrylate (Compound E.O. 34)

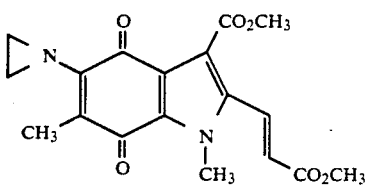

(45) Methyl 3-methoxycarbonyl-1-methyl-5-morpholino-2-[1H-indole-4,7-dione]acrylate (Compound E.O. 55)

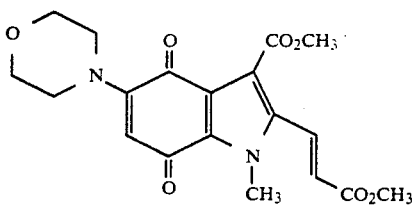

(46) Methyl 5-ethylamino-3-methoxycarbonyl-1-methyl-2-[1H-indole-4,7-dione]acrylate (Compound E.O. 57)

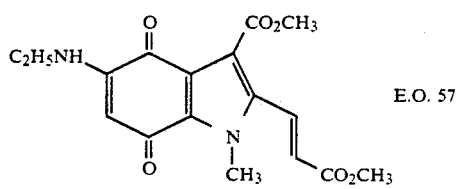

E.O. 57

These compounds, indoloquinone E.O. 29 excluded, can be readily prepared from the compound 18 (E.O. 14), which is an intermediate in the reaction scheme III given above for the preparation of the compound E.O. 7. Compound E.O. 29 can be synthesized from indole derivative 15 (scheme III) following reduction ($NO_2$ group) and oxidation pathways (Fremy's salt).

Compound E.O. 29 has also been proven to be a suitable starting indoloquinone for the introduction of several $R_5$-substituents.

Details for the preparation of the compounds E.O. 1 to E.O. 6, and E.O. 8 to E.O. 13, from compound E.O. 7 and their characterization are given in the following examples 2 to 13. Details for the synthesis of the indoloquinones E.O. 39, E.O. 41 and E.O. 64 in the examples 14, 15 and 16. Details of the preparation of the compound E.O. 22 from compound 18 (E.O. 14) and its characterization is given in example 17.

Examples 2 to 13, and 14, 15 and 16 are divided into four groups:

A —Synthesis of compounds E.O. 1 to E.O. 3, E.O. 10 and E.O. 13, in which both hydroxyl groups in E.O. 7 are substituted by functional groups, which possess good leaving group properties;

B —Syntheses of compounds E.O. 4 to E.O. 6, by treatment of compound E.O. 1 with an excess of a primary or secondary amine; and C —Syntheses of compounds E.O. 8, E.O. 9, E.O. 11 and E.O. 12 by treatment of compound E.O. 7 with an excess of a secondary amine; and D —Syntheses of compounds E.O. 39, E.O. 41 and E.O. 64 via reductive alkylation pathways using indoloquinone E.O. 1 as substrate.

GROUP A

EXAMPLE 2

3-Acetoxymethyl-5-methoxy-1-methyl-2-[1H-indole-4,7-dione]-prop-β-en-α-yl acetate (E.O. 1)

To a solution of 0.24 g (0.87 mmol) of E.O. 7 in $CH_2Cl_2$ (35 ml) were added pyridine (7 ml) and acetic anhydride (5 ml). After stirring for 6 h at room temperature the mixture was poured into ice. The water layer was extracted with $CHCl_3$(3×). The combined organic layers were washed with cold (0° C.) 3N HCl (3×) and sat. $NaHCO_3$ aq. dried over $MgSO_4$ and evaporated under reduced pressure. The residue was submitted to flash column chromatography ($SiO_2$, $CH_2Cl_2$/acetone 95/5), affording 0.205 g (65%) of E.O. 1 as orange crystals.

M.p. 167°-168° C. (MeOH). IR(KBr): 1725 (ester C=O), 1680 (quinone C=O), 1600 (quinone C=C).

$^1H$ NMR δ($CDCl_3$): 6.49 (dt, 1H, J=16.1 Hz, J=1.4 Hz, CH=CHCH$_2$OH), 6.11 (dt, 1H, J=16.1 Hz and J=5.8 Hz, CH=CHCH$_2$OH), 5.66 (s, 1H, H-6), 5.23 (s, 2H, ArCH$_2$), 4.74 (dd, 2H, J=5.8 Hz and J=1.4 Hz), 3.93 (s, 3H), 3.80 (s, 3H), 2.10 (s, 3H, COCH$_3$) and 2.04 (s, 3H, COCH$_3$).

An exact mass determination gave 361.1133; $C_{18}H_{19}N_1O_7$ requires 361.1105 (7.8).

EXAMPLE 3

Methyl 5-methoxy-3-methoxycarbonyloxymethyl-1-methyl-2-[1H-indole-4,7-dione]prop-β-en-α-yl carbonate (E.O. 2)

To a chilled solution (−10° C.) of 72 mg (0.26 mmol) of E.O. 7 in a mixture of anhydrous pyridine (12 ml) and anhydrous $CH_2Cl_2$ (45 ml) was added, while stirring, methyl chloroformate (2.5 ml) dissolved in $CH_2Cl_2$ (5 ml). During the addition the temperature was kept below −10° C. Thereupon the reaction mixture was stirred overnight at room temperature. The work-up and purification was essentially the same as described for E.O. 1, affording 60 mg (59%) E.O. 2 (orange crystals).

M.p. 156°-157° C. (MeOH). IR(KBr): 1740 (ester C=O), 1680 (quinone C=O), 1600 (quinone C=C).

$^1H$ NMR δ($CDCl_3$): 6.54 (dt, 1H, J=16.1 Hz and J=1.4 Hz, CH=CHCH$_2$OH), 6.17 (dt, 1H, J=16.1 Hz and J=5.6 Hz, CH=CH—CH$_2$OH), 5.65 (s, 1H, H-6), 5.32 (s, 2H, ArCH$_2$), 4.81 (dd, 2H, J=1.4 Hz and J=5.6 Hz, CH=CHCH$_2$), 3.93 (s, 3H), 3.81 (s, 3H), 3.79 (s, 3H), and 3.77 (s, 3H).

An exact mass determination gave 393.1097; $C_{18}H_{19}N_1O_9$ requires 393.1134 (9.4).

EXAMPLE 4

3-Carbamoyloxymethyl-5-methoxy-1-methyl-2-[1H-indole-4,7-dione]prop-β-en-α-yl carbamate (E.O. 3)

To a chilled solution (0° C.) of 0.150 g (0.54 mmol) of crude E.O. 7 in a mixture of anhydrous pyridine (30 ml) and anhydrous $CH_2Cl_2$ (75 ml) was added phenyl chloroformate (6 ml) while stirring and keeping the temperature below 0° C. Thereupon the whole mixture was stirred at room temperature for 1 h. The reaction mixture was worked up according to the procedure described for E.O. 1 and E.O. 2. The crude product obtained after evaporation of the volatiles was purified by flash column chromatography ($SiO_2$, $CH_2Cl_2$/acetone 95/5), yielding 181 mg (65%) of phenyl 4,7-dioxo-5-methoxy-N-methyl-3-phenoxycarbonyloxymethyl-2-indoleprop-β-en-α-yl carbonate. The latter product was dissolved in $CH_2Cl_2$ (40 ml). Ammonia gas was passed into this solution, while chilling in a Dry-Ice/ethanol bath for 0.5 h. The Dry-Ice/ethanol bath was removed and the reaction mixture was stirred at room temperature for 2 h. The excess of ammonia was removed by warming on a water bath. Red crystals separated, which were collected by filtration. The crystals were washed with $CH_2Cl_2$ and ethanol (abs). After drying in vacuo at 50° C., 60 mg of E.O. 3 (47% based on E.O. 7) were obtained.

M.p.>300° C. IR(KBr): 3440, 3380, 3340, 3280 and 3210 ($NH_2$), 1720 and 1695 (carbamate C=O), 1675 (quinone C=O), 1605 (quinone C=C). $^1$H NMR δ(DMSO-d$_6$), 6.68 (d, 1H, J=16.1 Hz, CH=CHCH$_2$OH), 6.49 (br, s, 4H, NH$_2$), 6.20 (dt, 1H, J=16.1 Hz and J=5.5 Hz, CH=CHCH$_2$OH), 5.86 (s, 1H, H-6), 5.04 (s, 2H, Ar CH$_2$), 4.67 (d, 2H, J=5.5 Hz, CH=CHCH$_2$), 3.92 (s, 3H), 3.79 (s, 3H).

An exact mass determination gave 363.1047; $C_{16}H_{17}N_3O_7$ requires 363.1066 (5.2).

EXAMPLE 5

3-(N-chloroethylcarbamoyloxymethyl)-5-methoxy-1-methyl-2-[1H-indole-4,7-dione]prop-β-en-α-yl N-chloroethylcarbamate (E.O. 13)

A solution of 94 mg (0.34 mmol) of E.O. 7 in anhydrous $CH_2Cl_2$ (30 ml) was refluxed with N-chloroethylisocyanate (10 ml) for 48 h. After evaporation of the solvent and the excess of N-chloroethylisocyanate in vacuo, the residue was submitted to flash column chromatography ($SiO_2$, $CH_2Cl_2$/acetone 95/5) giving 95 mg (60%) of E.O. 13 (purple crystals).

M.p. 171°-172° C. IR(KBr): 3300 (NH), 1690 (carbamate C=O), 1670 (shoulder: quinone C=O), 1600 (quinone C=C).

$^1$H NMR δ(CDCl$_3$): 6.51 (d, 1H, J=16.1 Hz, CH=CHCH$_2$OH), 6.16 (dt, 1H, J=5.4 Hz and J=16.1 Hz), 5.65 (s, 1H, H-6), 5.27 (s, 2H, Ar CH$_2$), 5.16 (br s, 2H, NH), 3.93 (s, 3H), 3.80 (s, 3.4–3.7 (m, 8H)).

EXAMPLE 6

5-Methoxy-3-methoxymethyl-1-methyl-2-[1H-indole-4,7-dione]prop-β-en-α-yl N-chloroethylcarbamate (E.O. 10)

A solution of 90 mg (0.325 mmol) of E.O. 7 in anhydrous $CH_2Cl_2$ (30 ml) was refluxed with N-chloroethylisocyanate (10 ml) for 48 h. After evaporation of the solvent and the excess of N-chloroethylisocyanate in vacuo, the residue was crystallized from methanol. The orange crystals were collected by filtration and dried in vacuo.

Yield: 56 mg (48%). M.p. 176°-177° C.

IR(KBr): 3300 (NH), 1700 (carbamate C=O), 1675 (quinone C=O), 1600 (quinone C=C).

$^1$H NMR δ(CDCl$_3$): 6.35–6.55 (m, 2H, CH=CHCH$_2$), 5.64 (s, 1H, H-6), 5.18 (br s, 1H, NH), 4.78 (d, 2H, J=3.7 Hz, CH=CHCH$_2$), 4.61 (s, 2H, ArOCH$_2$), 3.94 (s, 3H), 3.80 (s, 3H), 3.45–3.7 (m, 4H,

CNHCH$_2$CH$_2$Cl), 3.39 (s, 3H, CH$_2$OCH$_3$).

GROUP B

EXAMPLE 7

3-Acetoxymethyl-5-aziridino-1-methyl-2-[1H-indole-4,7-dione]prop-β-en-α-yl acetate (E.O. 4)

A suspension of 90 mg (0.25 mmol) of E.O. 2 in anhydrous methanol was heated with aziridine (3.5 ml) at 40°–45° C. for 2 h. The residue obtained, after the evaporation of the solvent and the excess aziridine in vacuo, was submitted to flash column chromatography ($SiO_2$, $CH_2Cl_2$/acetone 7/3), affording 78 mg (84%) of E.O. 4 (reddish crystals).

M.p. 195°–196° C. (MeOH). IR(KBr): 1730 (ester C=O), 1667 (quinone C=O), 1590 (quinone C=C). $^1$H NMR δ(CDCl$_3$): 6.49 (dt, 1H, J=16.1 Hz and J=1.4 Hz, CH=CH—CH$_2$), 6.10 (dt, 1H, J=16.1 Hz and J=5.8 Hz, CH=CH—CH$_2$), 5.80 (s, 1H, H-6), 5.24 (s, 2H, Ar CH$_2$), 4.74 (dd, 2H, J=1.4 Hz and J=5.8 Hz), 3.92 (s, 3H, N—CH$_3$), 2.19 (s, 4H, —CH$_2$N), 2.10 and 2.06 (s, 3H, OCOCH$_3$).

An exact mass determination gave 372.1345; $C_{19}H_{20}N_2O_6$ requires 372.1369 (6.5).

EXAMPLE 8

3-Acetoxymethyl-5-(2-hydroxyethyl-1-amino)-1-methyl-2-[1H-indole-4,7-dione]prop-β-en-α-yl acetate (E.O. 5)

To a solution of 40 mg (0.111 mmol) of E.O. 1 in anhydrous methanol (60 ml) was added ethanolamine (1 ml). The whole mixture was stirred for 6 h at room temperature. Thereupon it was poured into water and extracted with CHCl$_3$ (5×). The combined organic layers were washed with sat. NaCl aq. and dried over Na$_2$SO$_4$. After evaporation of the volatiles the residue was submitted to flash column chromatography ($SiO_2$, $CH_2Cl_2$/acetone 7/3).

Yield: 30 mg (70%) of purple crystals.

M.p. 198°-200° C. (MeOH). IR(KBr): 3200-3600 (OH), 3360 (NH), 1710 (ester C=O), 1650 (quinone C=O), 1595 (quinone C=C).

$^1$H NMR δ(CDCl$_3$): 6.49 (dt, 1H, J=16.1 Hz and J=1.4 Hz, CH=CHCH$_2$), 7.16 (br t, 1H, NH), 6.09 (dt, 1H, J=16.1 Hz and J=1.4 Hz, CH=CHCH$_2$), 5.23 (s, 3H, H-6 and Ar CH$_2$), 4.74 (dd, 2H, J=5.9 Hz and J=1.4 Hz, CH=CH—CH$_2$), 3.96 (s, 3H, N—CH$_3$), 3.80-3.95 (m, 2H, CH$_2$—O), 3.25-3.35 (m, 2H, CH$_2$N), 2.11 and 2.06 (s, 3H, OCOCH$_3$), 1.79 (br t, 1H, OH).

An exact mass determination gave 390.1385; $C_{19}H_{22}N_2O_7$ requires 390.1344 (10.5).

EXAMPLE 9

3-Acetoxymethyl-5-(2,3-dihydroxypropyl-1-amino)-1-methyl-2-[1H-indole-4,7-dione]prop-β-en-α-yl acetate (E.O. 6)

To a solution of 90 mg (0.25 mmol) of E.O. 3 in anhydrous methanol (110 ml) was added 1-amino-2,3-dihydroxypropane (0.45 g). The whole mixture was heated at 45°–50° C. for 10 h. The work-up was essentially the same as described for E.O. 5. Flash column chromatography ($SiO_2$, $CH_2Cl_2$/acetone 6/4) gave 65 mg (62%) of E.O. 6 (purple crystals).

M.p. 180°–181° C. (MeOH). IR(KBr): 3100–3600 (NH and OH), 1720 (ester C=O), 1600 (quinone C=O), 1590 (quinone C=C).

$^1$H NMR δ(CDCl$_3$): 6.47 (dt, 1H, J=16.0 Hz and J=1.3 Hz), 6.26 (br t, 1H, NH), 6.09 (dt, 1H, J=16.0 Hz and J=5.8 Hz, CH=CHCH$_2$), 5.21 (s, 1H, H-6), 5.19 (s, 2H, Ar CH$_2$), 4.74 (dd, 2H, J=5.8 Hz and J=1.3 Hz), 3.83–4.07 (m, 1H, CHOH), 3.93 (s, 3H, N—CH$_3$), 3.53–3.83 (m, 2H, CH$_2$OH), 3.10–3.30 (m, 2H, CH$_2$N), 2.79 (d, 1H, J=4.2 Hz, CHOH), 2.18 (br t, 1H, CH$_2$OH), 2.11 and 2.05 (s, 3H, OCOCH$_3$).

GROUP C

EXAMPLE 10

3-Hydroxymethyl-1-methyl-5-propyleneamino-2-[1H-indole-4,7-dione]prop-β-en-α-ol (E.O. 8)

A solution of 55.5 mg (0.20 mmol) of E.O. 7 in anhydrous methanol was heated with propyleneimine (1 ml) at 60°–65° C. for 1 h. After stirring overnight the solvent and the excess of propyleneimine were removed in vacuo. From the residue obtained indoloquinone E.O. 8 was isolated by flash column chromatography ($SiO_2$, $CH_2Cl_2$/acetone 7/3).

Yield: 44 mg (73%) (red crystals). M.p. 122.5°–124° C. (MeOH). IR(KBr): 3100–3600 (OH), 1660 (quinone C=O), 1590 (quinone C=C).

$^1$H NMR (100 MHz) δ(CDCl$_3$): 6.49 (dt, 1H, J=1.4 Hz and J=16 Hz, CH=CHCH$_2$OH), 6.13 (dt, 1H, J=4.5 Hz and J=16 Hz, CH=CHCH$_2$OH), 5.77 (s, 1H, H-6), 4.71 (br d, 2H, J=6.5 Hz, Ar CH$_2$OH), 4.4 (br s, 2H, CH=CHCH$_2$OH), 4.25 (br t, 1H, J=6.5 Hz, Ar CH$_2$OH), 3.91 (s, 3H, N—CH$_3$), 2–2.5 (m, 4H, CH=CHCH$_2$OH, CH$_2$N, CH—N), 1.43 (d, 3H, J=5 Hz, CHCH$_3$).

An exact mass determination gave 302.1294; $C_{16}H_{18}N_2O_4$ requires 302.1267 (9).

EXAMPLE 11

5-Aziridino-3-hydroxymethyl-1-methyl-2-[1H-indole-4,7-dione]prop-β-en-α-ol (E.O. 9)

A solution of 80 mg (0.289 mmol) of E.O. 7 in anhydrous methanol (30 ml) was heated with aziridine (1 ml) at 40°–45° C. for 1 h. The work-up proceeded analogously to that described for E.O. 8, affording, after column chromatography ($SiO_2$, $CH_2Cl_2$/acetone 6/4), 58 mg (70%) of indoloquinone E.O. 9 (purple crystals).

M.p. 160°–169° C. IR(KBr): 3100–3600 (OH), 1660 (quinone C=O), 1595 (quinone C=C).

$^1$H NMR δ(CDCl$_3$): 6.4–6.55 (m, 1H, CH=CHCH$_2$), 6.12 (dt, 1H, J=4.6 Hz and J=16.0 Hz, CH=CHCH$_2$). 5.79 (s, 1H, H-6), 4.68 (d, 2H, J=7.1 Hz, Ar CH$_2$OH), 4.38 (m, 2H, CH=CHCH$_2$OH), 4.13 (t, 1H, J=7.1 Hz, Ar CH$_2$OH), 3.90 (s, 3H, N—CH$_3$), 2.20 (s, 4H, CH$_2$N), 1.76 (t, 1H, J=5.6 Hz, CH=CHCH$_2$OH).

An exact mass determination gave 288.1082; $C_{15}H_{16}N_2O_4$ requires 288.1110 (9.9).

EXAMPLE 12

3-Hydroxymethyl-5-(4-hydroxypiperidino)-1-methyl-2-[1H-indole-4,7-dione]prop-β-en-α-ol (E.O. 11)

To a solution of 92 mg (0.33 mmol) of E.O. 7 in anhydrous methanol (30 ml) were added 4-hydroxypiperidine (100 mg), triethylamine (2 ml) and potassium carbonate (7 mg). The whole mixture was refluxed for 16 h. Thereupon the volatiles were removed at reduced pressure. The residue was mixed with silicagel and submitted to flash column chromatography ($SiO_2$, $CH_2Cl_2$/acetone 6/4).

Yield: 72 mg (63%) of indoloquinone E.O. 11 (black crystals).

M.p. 180°–181° C. (MeOH). IR(KBr): 3100–3600 (OH), 1660 (quinone C=O), 1595 (quinone C=C).

$^1$H NMR δ(DMSO-d$_6$): 6.35–6.6 (m, 2H, CH=CH) 5.50 (s, 1H, H-6), 5.04 (t, 1H, J=5.3 Hz, CH=CHCH$_2$OH), 4.79 (d, 1H, J=4.1 Hz, CHOH), 4.72 (t, 1H, J=5.1 Hz, Ar CH$_2$OH), 4.56 (d, 2H, J=5.0 Hz, Ar CH$_2$OH), 4.20 (m, 2H, CH=CHCH$_2$), 3.90 (s, 3H, NCH$_3$), 3.6–3.8 [m, 3H, CHOH, NCH$_2$(a)], 3.0–3.2 [m, 2H, NCH$_2$(e)], 1.7–1.9 [m, 2H, CH$_2$CHOH (a)], 1.4–1.6 [m, 2H, CH$_2$CHOH (e)].

EXAMPLE 13

3-Hydroxymethyl-1-methyl-5-morpholino-2-[1H-indole-4,7-dione]prop-β-en-α-ol (E.O. 12)

To a solution of 90 mg (0.325 mmol) of indoloquinone E.O. 7 in anhydrous methanol (30 ml) were added morpholine (86 mg), triethylamine (2 ml) and potassium carbonate (10 mg). The whole mixture was refluxed for 16 h.

Work-up was essentially the same as described for E.O. 11. Yield: 56 mg (52%) (claret coloured crystals). M.p. 204°–205° C. (MeOH). IR(KBr): 3100–3600 (OH), 1660 (quinone C=O).

$^1$H NMR δ(DMSO-d$_6$): 6.4–6.6 (m, 2H, CH=CH), 5.50 (s, 1H, H-6), 5.05 (t, 1H, J=5.3 Hz, CH=CHCH$_2$OH), 4.71 (t, 1H, J=5.1 Hz, Ar CH$_2$OH), 4.55 (d, 2H, J=5.0 Hz Ar CH$_2$OH), 4.20 (m, 2H, CH=CH$_2$OH), 3.89 (s, 3H, NCH$_3$), 3.72 (m, 4H, O—CH$_2$).

An exact mass determination gave 332.1344; $C_{17}H_{20}N_2O_5$ requires 332.1372 (8.6).

Compounds E.O. 6, E.O. 10, E.O. 11 and E.O. 13 could not be analyzed by Electron Impact Mass Spectrometry either due to their low volatility or their instability at high temperatures. In consequence no accurate mass determination of the latter compounds are available.

The field desorption mass spectrum of E.O. 6 showed a molecular ion peak (M+) at m/e 420. The Field desorption mass spectrum of E.O. 13 showed very intensive peaks at m/e 487 and 489.

GROUP D

EXAMPLE 14

5-Methoxy-1-methyl-3-(N-phenylaminomethyl)-2-[1H-indole-4,7-dione]prop-β-en-α-yl acetate (E.O. 39)

To a vigorously stirred solution of 81 mg (0.22 mmol) of E.O. 1 and 800 mg of aniline (8.6 mmol) in a mixture of methylene chloride (24 ml) and methanol (16 ml) was added a solution of $Na_2S_2O_4$ (2.4 g) in water (20 ml).

Stirring was continued for 2 minutes. Thereupon the organic layer was separated and washed twice with sat. aq. NaCl. After drying over Na$_2$SO$_4$ the solution was evaporated under reduced pressure.

The residue was submitted to flash column chromatography using SiO$_2$ as stationary phase and consecutively methylene chloride—to remove the excess of aniline—and a mixture of methylene chloride and acetone (95/5) as eluens, affording 71 mg (80%) of E.O. 39 as red crystals.

Mp: 153°-154° C. (methanol).

IR (KBr): 3350 (NH), 1735 (ester C=O), 1670 (quinone C=O), 1600 (quinone C=C).

$^1$H NMR δ(CDCl$_3$): 7.06-7.13 (m,2H, phenyl-H), 6.5-6.7 (m, 4H, phenyl-H and —CH=CHCH$_2$—), 6.15 (dt, J=16 Hz, and J=5.8 Hz, —CH=CHCH$_2$—), 5.64 (s, 1H, H-6), 4.88 (br s, 1H, NH), 4.79 (dd, 2H, J=1.3 Hz and 5.8 Hz, —CH=CHCH$_2$), 4.37 (s, 2H, ArCH$_2$—), 3.88 (s, 3H) and 3.81 (s, 3H), 2.12 (s, 3H, —COCH$_3$).

An exact mass determination gave 394.1527; C$_{22}$H$_{22}$N$_2$O$_5$ requires 394.1529 (0.5).

EXAMPLE 15

Methoxy-1,3-dimethyl-2-[1H-indole-4,7-dione]prop-β-en-α-yl acetate (E.O. 41)

To a vigorously stirred solution of 86 mg (0.24 mmol) of E.O. 1 in a mixture of methylene chloride (18 ml), methanol (9 ml) and triethylamine (3 ml) was added a solution of Na$_2$S$_2$O$_4$ (1.5 g) in water (15 ml). Stirring was continued for five minutes. Thereupon the organic layer was separated and washed twice with sat. aq. NaCl. After drying over MgSO$_4$ the solution was evaporated under reduced pressure.

The residue was submitted to flash column chromatography (SiO$_2$, CH$_2$Cl$_2$/acetone: 95/5), affording 58 mg (80%) of E.O. 41 as claret crystals.

Mp: 166°-167° C. (MeOH).

IR (CHCl$_3$): 1735 (ester C=O), 1670 (quinone C=O), 1600 (quinone C=C).

$^1$H NMR δ(CDCl$_3$): 6.51 (d, 1H, J=16 Hz, —CH=CHCH$_2$), 6.10 (dt, 1H, J=16 and 6H, —CH=CHCH$_2$—), 5.63 (s, 1H, H-6), 4.75 (d, 2H, J=6 Hz, —CH=CHCH$_2$—), 3.94 (s, 3H) and 3.80 (s, 3H), 2.39 (s, 3H, Ar—CH$_3$), 2.12 (s, 3H, COCH$_3$).

An exact mass determination gave 303.1094; C$_{16}$H$_{17}$NO$_5$ requires 303.1107 (4.2).

EXAMPLE 16

O-Ethyl 5-methoxy-1-methyl-2-[1H-indole-4,7-dione]prop-β-en-α-yl dithiocarbonate (E.O. 64)

To a vigorously stirred solution of 61 mg (0.17 mmol) of E.O. 1 and 272 mg (1.7 mmol) of potassium ethylxanthate in a mixture of methylene chloride (18 ml) and methanol (12 ml) was added a solution of Na$_2$S$_2$O$_4$ (1.8 g) in water (15 ml). Stirring was continued for ten minutes. Thereupon the organic layer was separated and washed twice with sat. aq. NaCl. After drying over MgSO$_4$ the solution was evaporated under reduced pressure. The residue was submitted to flash column chromatography (SiO$_2$, CH$_2$Cl$_2$/acetone 95/5), affording 65 mg (89%) of E.O. 64 as a red oil.

IR (CHCl$_3$): 1740 (ester C=O), 1672 (quinone C=O), 1600 (quinone C=C).

$^1$H NMR δ(CDCl$_3$): 6.52 (d, 1H, J=16.2 Hz, —CH=CHCH$_2$), 6.17 (dt, 1H, J=16.2 Hz, and J=5.7 Hz, —CH=CHCH$_2$—), 5.65 (s, 1H, H-6), 4.76 (dd, 2H, J=5.7 Hz and J=1.1 Hz, —CH=CHCH$_2$), 4.6-4.8 (m, 4H), 3.93 (s, 3H) and 3.80 (s, 3H), 2.12 (s, 3H, —COCH$_3$), 1.42 (t, 3H, J=7.1 Hz, CH$_2$CH$_3$).

EXAMPLE 17

Methyl 5-aziridino-3-methoxycarbonyl-1-methyl-2-[1H-indole-4,7-dione]acrylate (E.O. 22)

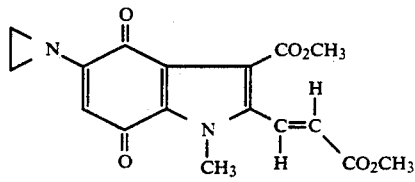

A suspension of methyl 5-methoxy-3-methoxycarbonyl-N-methyl-4,7-dioxo-2-indoleacrylate (18) (600 mg, 1.8 mmol) in anhydrous methanol (200 ml) was heated with aziridine (5 ml) at 45°-50° C. for 5 h. The residue obtained, after the evaporation of the solvent and the excess of aziridine in vacuo, was submitted to flash column chromatography (SiO$_2$, CH$_2$Cl$_2$/acetone 95/5), affording 570 mg (92%) of E.O. 22 (orange crystals).

M.p. 204°-206° C. (MeOH). IR(KBr): 1720 (ester C=O), 1690 (quinone C=O), 1590 (quinone C=C).

$^1$H NMR δ(CDCl$_3$): 7.60 (d, 1H, J=16.2 Hz, CH=CHCO$_2$Me), 6.40 (d, 1H, J=16.2 Hz, CH=CHCO$_2$Me), 5.85 (s, 1H, H-6), 4.04 (s, 3H), 3.94 (s, 3H), 3.79 (s, 3H) and 2.21 (s, 4H, —CH$_2$N).

An exact mass determination gave 344.0992; C$_{17}$H$_{16}$N$_2$O$_6$ requires 344.1008 (4.6).

Elemental analysis: Calculated for C$_{17}$H$_{16}$N$_2$O$_6$=C, 59.29; H, 4.69. Found: C, 59.17; H, 4.68.

EXAMPLE 18

3-Hydroxymethyl-5-methoxy-1-methyl-2-[1H-indole-4,7-dione]prop-β-en-α-yl acetate (E.O. 1A)

To a solution of 40 mg (0.11 mmol) of E.O. 1 in acetone (15 ml) was carefully added 10N H$_2$SO$_4$ (20 ml). The whole mixture was stirred for 15 min at room temperature. Thereupon the reaction mixture, containing for the greater part, the indoloquinones E.O. 1A and E.O. 7, was poured into a sat. aq. solution of NaHCO$_3$. The water layer was extracted with CHCl$_3$. The combined extracts were dried over MgSO$_4$. The residue obtained after the evaporation of the solvent was submitted to flash column chromatography (SiO$_2$, CH$_2$Cl$_2$/acetone 95/5), affording 7 mg (20%) of indoloquinone E.O. 1A (red crystals).

M.p. 168°-169° C. (MeOH).

IR (KBr): 3360 (OH), 1735 (ester C=O), 1670 (quinone C=O) and 1595 (quinone C=C).

$^1$NMR δ(CDCl$_3$): 6.48 (dt, 1H, J=16.1 Hz and J=1.4 Hz, CH=CHCH$_2$OAc), 6.05 (dt, 1H, J=16.0 Hz and J=5.8 Hz, CH=CHCH$_2$OH), 5.67 (s, 1H, H-6), 4.75 (dd, 2H, J=5.8 Hz and J=1.4 Hz, CH=CHCH$_2$), 4.66 (d, 2H, J=7 Hz, ArCH$_2$—), 3.96 (t, 1H, J=7 Hz, OH), 3.90 (s, 3H), 3.82 (s, 3H) and 2.10 (s, 3H, —COCH$_3$).

An exact mass determination gave: 319.1095; C$_{16}$H$_{17}$NO$_6$ requires 319.1056 (0.9).

EXAMPLE 19

3-Acetoxymethyl-5-methoxy-1-methyl-2-[1H-indole-4,7-dione]-prop-β-en-α-ol (E.O. 1B)

A solution of 100 mg (0.275 mmol) in a mixture of methanol (70 ml) and NEt$_3$ (1 ml) was refluxed for 35 min. Thereupon the solvent was removed in vacuo. The residue obtained was submitted to flash column chromatography (SiO$_2$; CH$_2$Cl$_2$/acetone 7/3) affording 61 mg (70%) of E.O. 1B.

M.p. 183°–185° C. (MeOH).

IR (KBr): 3480 (OH), 1715 (ester C=O), 1670 (quinone C=O), 1595 (quinone C=C).

$^1$NMR δ(CDCl$_3$): 6.51 (d, 1H, J=16.1 Hz, CH=CHCH$_2$OAc), 6.19 (dt, 1H, J=16.1 Hz and J=4.6 Hz, CH=CHCH$_2$OH), 5.65 (s, 1H, H-6), 5.24 (s, 2H, ArCH$_2$—), 4.39 (m, 2H, CH=CHCH$_2$), 3.93 (s, 3H), 3.80 (s, 3H) and 2.04 (s, 3H, —COCH$_3$), 3.93 (t, 1H, J=5.4 Hz, OH).

An exact mass determination gave: 319.1095; C$_{16}$H$_{17}$NO$_6$ requires 319.1056 (0.9).

EXAMPLE 20

3-Acetoxymethyl-5-aziridino-1-methyl-2-[1H-indole-4,7-dione]-prop-β-en-α-ol (E.O. 4A)

A solution of 155 mg (0.42 mmol) E.O. 4 in a mixture of anhydrous methanol (120 ml) and NEt$_3$ (2 ml) was heated at 50° C. for 1 h. Thereupon the solution was evaporated. The residue obtained, for the greater part a mixture of indoloquinone E.O. 4A and E.O. 9 was submitted to flash column chromatography (SiO$_2$; CH$_2$Cl$_2$/acetone 7/3), affording 90 mg (64%) of compound E.O. 4A (red crystals).

M.p. 193°–195° C. (MeOH; dec.).

IR (KBr): 3360 (OH), 1725 (ester C=O), 1665 (quinone C=O), 1575 (quinone C=C).

$^1$NMR δ(CDCl$_3$): 6.51 (dt, 1H, J=16.1 Hz and J=1.8 Hz, CH=CHCH$_2$OH), 6.18 (dt, 1H, J=16.1 Hz and J=4.6 Hz, CH=CHCH$_2$OH), 5.79 (s, 1H, H-6), 5.25 (s, 2H, ArCH$_2$—), 4.38 (m, 2H, CH=CHCH$_2$), 3.92 (s, 3H, NCH$_3$), 2.19 (s, 4H, —CH$_2$N—), 2.06 (s, 3H, —COCH$_3$), 1.78 (t, 1H, J=5.5 Hz, OH).

An exact mass determination gave: 330.1305; C$_{17}$H$_{18}$N$_2$O$_5$ requires 330.1216 (27).

EXAMPLE 21

3-Acetoxymethyl-1,6-dimethyl-5-methoxy-2-[1H-indole-4,7-dione]prop-β-en-α-yl acetate (E.O. 33)

The synthesis of this compound from indoloquinone E.O. 18 proceeded similar to that described for indoloquinone E.O. 1 from E.O. 7.

Yield: 85%; Orange red crystals.

M.p. 185°–187° C.

IR (KBr): 1725 (ester C=O), 1660 (quinone C=O), 1600 (quinone C=C).

$^1$NMR δ(CDCl$_3$): 6.50 (dt, 1H, J=16.1 Hz and J=1.3 Hz, CH=CHCH$_2$OAc), 6.10 (dt, 1H, J=16.1 Hz and J=5.8 Hz, CH=CHCH$_2$OH), 5.23 (s, 2H, ArCH$_2$—), 4.74 (dd, 2H, J=5.8 Hz and J=1.3 Hz, CH=CHCH$_2$), 4.00, 3.92, 2.10, 2.05 and 1.94 (s, 3H).

An exact mass determination gave: 375.1317; C$_{19}$H$_{21}$NO$_7$ requires 375.1318 (0.3)

EXAMPLE 22

3-Acetoxymethyl-5-aziridino-1,6-dimethyl-2-[1H-indole-4,7-dione]prop-β-en-α-yl acetate (E.O. 35)

The synthesis of this compound from indoloquinone E.O. 33 proceeded similar to that described for indoloquinone E.O. 4 from E.O. 1.

Yield: 82%; purple crystals.

M.p. 200°–202° C. (MeOH).

IR (KBr): 1725 (ester C=O), 1660 (quinone C=O), 1590 (quinone C=C).

$^1$NMR δ(CDCl$_3$): 6.51 (dt, 1H, J=16.1 Hz and J=1.3 Hz, CH=CHCH$_2$—), 6.11 (dt, 1H, J=16.1 Hz and J=5.8 Hz, CH=CHCH$_2$—), 5.26 (s, 2H, ArCH$_2$—), 4.76 (dd, 2H, J=5.8 and J=1.3 Hz, CH=CHCH$_2$), 3.94 (s, 3H, NCH$_3$), 2.31 (s, 4H, —CH$_2$N—), 2.12, 2.07 and 2.06 (s, 3H).

An exact mass determination gave: 386.1478; C$_{20}$H$_{22}$N$_2$O$_6$ requires 386.1478 (0.0)

EXAMPLE 23

3-Benzoxymethyl-5-methoxy-1-methyl-2-[1H-indole-4,7-dione]prop-β-en-α-yl benzoate (E.O. 36)

A solution of 70 mg (0.253 mmol) of indoloquinone E.O. 7 and 80 mg (0.633 mmol) of benzoylchloride in a mixture of CH$_2$CL$_2$ (anh.; 10 ml) and pyridine (1 ml) was refluxed for 3 h. Thereupon the reaction mixture was cooled, diluted with an additional amount of CH$_2$CL$_2$ and washed with cold aq. 3N HCl (5×). After drying over MgSO$_4$ the solvents were removed in vacuo. The residue obtained was submitted to flash column chromatography (SiO$_2$; CH$_2$Cl$_2$/acetone 95/5), affording 52 mg (43%) of compound E.O. 36 (red crystals).

M.p. 166°–168° C. (MeOH).

IR (CHCl$_3$): 1715 (ester C=O), 1670 (quinone C=O), 1595 (quinone C=C).

$^1$NMR δ(CDCl$_3$): 7.9-8.1 (m, 4H, phenyl-H), 7.2-7.6 (m, 6H, phenyl-H) 6.67 (dt, 1H, J=16.1 Hz and J=1.4 Hz, CH=CHCH$_2$—), 6.34 (dt, 1H, J=16.1 Hz and J=5.6 Hz, CH=CHCH$_2$—), 5.68 (s, 1H, H-6), 5.55 (s, 2H, ArCH$_2$—), 4.99 (dd, 2H, J=5.6 Hz and J=1.4 Hz, CH=CHCH$_2$), 3.97 (s, 3H) and 3.80 (s, 3H). FD MS: m/e 485 (M+).

EXAMPLE 24

3-[N-butylcarbamoyloxymethyl]-5-methoxy-1-methyl-2-[1H-indole-4,7-dione]prop-β-en-α-yl N-butylcarbamate (E.O. 37)

To a solution of 70 mg (0.253 mmol) in CH$_2$CL$_2$ (15 ml) were added K$_2$CO$_3$ (1 g) and n-butyl isocyanate (2 ml). The whole was refluxed for 4 h. After cooling the reaction mixture to room temperature, the excess of K$_2$CO$_3$ was removed by filtration. The residue, obtained after evaporation of the solvent and the excess of n-butyl isocyanate in vacuo, was sumitted to flash column chromatography (SiO$_2$; CH$_2$Cl$_2$/acetone 95/5), affording 76 mg (63%) of compound E.O. 37 (red crystals).

M.p. 190°–191° C. (MeOH).

IR (CHCl$_3$): 3300 (NH), 1685 (br.; carbamate C=O and quinone C=O), 1600 (quinone C=C).

$^1$NMR δ(CDCl$_3$): 6.51 (br.d, 1H, J=16.2 Hz, CH=CHCH$_2$—), 6.34 (dt, 1H, J=16.2 Hz and J=5.4 Hz, CH=CHCH$_2$—), 5.65 (s, 1H, H-6), 5.24 (s, 2H, ArCH$_2$—), 4.7-4.8 (br., 2H, NH), 4.73 (br. m, 2H, CH=CHCH$_2$), 3.93 (s, 3H) and 3.80 (s, 3H), 3.1–3.3 (m, 4H, NHCH$_2$—), 1.2–1.6 (m, 8H, —CH$_2$CH$_2$—CH$_3$), 0.8–1.0 (m, 6H, —CH$_2$CH$_3$)

FD MS: m/e 475 (M+).

EXAMPLE 25

5-Methoxy-1-methyl-3-[N-phenylcarbamoyloxymethyl]-2-[1H-indole-4,7-dione]prop-β-en-α-yl N-phenylcarbamate (E.O. 38)

To a solution of 70 mg (0.253 mmol) in CH$_2$CL$_2$ (15 ml) were added K$_2$CO$_3$ (1 g) and n-phenyl isocyanate (400 mg). The whole was refluxed for 17 h. After cooling the reaction mixture to room temperature, the excess of K$_2$CO$_3$ was removed by filtration. The residue, obtained after evaporation of the solvent and the excess of in vacuo, was suspended in methanol. The crystalline product was collected by filtration and finally submitted to flash column chromatography (SiO$_2$; CH$_2$Cl$_2$/acetone 95/5), affording 85 mg (50%) of compound E.O. 38 (dark red crystals).

M.p. 177°–178° C.

IR (CHCl$_3$): 3300 (NH), 1690 (br.; carbamate C=O and quinone C=O), 1600 (quinone C=C).

$^1$NMR δ(CDCl$_3$): 7.2–7.4 (m, 10H, phenyl-H), 6.4–6.6 (br. m, 1H, CH=CHCH$_2$—), 6.1–6.3 (br. m, 1H, CH=CHCH$_2$—), 5.65 (s, 1H, H-6), 5.30 (s, 2H, ArCH$_2$—), 5.0–5.3 (br. m, 2H, NH), 4.3–4.4 (m, 4H, CH$_2$C$_6$H$_5$), 4.7–4.8 (br. m, 2H, CH=CHCH$_2$), 3.91 and 3.80 (s, 3H).

Anal. Calcd for C$_{30}$H$_{29}$N$_3$O$_7$: C, 66.29; H, 5.38; N, 7.73. Found: C, 66.38; H, 5.39; N, 7.60.

EXAMPLE 26

3-Acetoxymethyl-5-[2-(N,N-dimethylamino)ethyl-1-amino]-1-methyl-2-[1H-indole-4,7-dione]prop-β-en-α-yl acetate (E.O. 47)

A)

3-hydroxymethyl-5-[2-(N,N-dimethylamino)ethyl-1-amino]-1-methyl-2-[1H-indole-4,7-dione]prop-β-en-α-ol A solution of 206 mg (0.744 mmol) of indoloquinone E.O. 7 in a mixture of methanol (60 ml) and H$_2$NCH$_2$CH$_2$N(CH$_3$)$_2$ (1 g) was refluxed for 2 h. After the evaporation of the solvent and the excess of the reagent, a crystalline mass was obtained which was employed in the next step without further purification.

B) The Synthesis of Indoloquinone E.O. 47

The crude reaction product was dissolved in a mixture of CH$_2$Cl$_2$ (28 ml) and pyridine (5.6 ml), containing DMAP (20 mg) and Ac$_2$O (4 ml). After stirring for 1 h at room temperature the solvents and the excess of the reagents were removed in vacuo. The residue thus obtained was submitted to flash column chromatography (SiO$_2$; CH$_2$Cl$_2$/MeOH 8/2), affording 260 mg (84%) of compound E.O. 47 (purple crystals).

M.p. 149°–150° C.

IR (KBr): 3310 (NH), 1730 (ester C=O), 1660 (quinone C=O), 1590 (quinone C=C).

$^1$NMR δ(CDCl$_3$): 6.4–6.6 (m, 2H, NH and CH=CHCH$_2$—), 6.10 (dt, 1H, J=16.1 Hz and J=5.9 Hz, CH=CHCH$_2$—), 5.24 (s, 2H, ArCH$_2$—), 5.17 (s, 1H, H-6), 4.75 (dd, 2H, J=5.9 and J=1.4 Hz, CH=CHCH$_2$), 3.97 (s, 3H, NCH$_3$), 3.05–3.2 (m, 2H, CH$_2$NH), 2.55 [t, 2H, J=6.1 Hz, —CH$_2$N(CH$_3$)$_2$], 2.23 [s, 6H, N(CH$_3$)$_2$], 2.11 and 2.06 (s, 3H).

Anal. Calcd for C$_{21}$H$_{27}$N$_3$O$_6$: C, 60.42; H, 6.52; N, 10.07. Found: C, 60.37; H, 6.55; N, 10.05.

EXAMPLE 27

3-Acetoxymethyl-5-[2-(N,N-dimethylamino)ethyl-1-amino]-1-methyl-2-[1H-indole-4,7-dione]prop-β-en-α-ol (E.O. 48)

A solution of 50 mg (0.120 mmol) of indoloquinone E.O. 47 in a mixture of methanol (anh.; 20 ml) and NEt$_3$ (0.5 ml) was heated for 1 h at 50° C. The residue obtained after the evaporation of the solvents in vacuo was submitted to flash column chromatography (SiO$_2$; CH$_2$Cl$_2$/MeOH 8/2), affording 25 mg (57%) of compound E.O. 48 (purple crystals).

M.p. 153°–155° C.

IR (KBr): 3100–3500 (NH and OH), 1730 (ester C=O), 1660 (quinone C=O), 1590 (quinone C=C).

$^1$NMR δ(CDCl$_3$): 6.50 (dt, 1H, 16.1 Hz and 1.5 Hz, CH=CHCH$_2$—), 6.42 (m, 1H, NH), 6.16 (dt, 1H, J=16.1 Hz and J=4.7 Hz, CH=CHCH$_2$—), 5.24 (s, 2H, ArCH$_2$—), 5.16 (s, 1H, H-6), 4.37 (dd, 2H, J=4.7 and J=1.6 Hz, CH=CHCH$_2$), 3.96 (s, 3H, NCH$_3$), 3.05–3.2 (m, 2H, CH$_2$NH), 2.55 [t, 2H, J=6.1 Hz, —CH$_2$N(CH$_3$)$_2$], 2.24 [s, 6H, N(CH$_3$)$_2$], 2.06 (s, 3H).

Anal. Calcd for C$_{21}$H$_{27}$N$_3$O$_6$: C, 60.42; H, 6.52; N, 10.07. Found: C, 60.37; H, 6.55; N, 10.05.

FD MS: m/e 375 (M+).

EXAMPLE 28

3-Hydroxymethyl-1-methyl-5-[2-pyridylethyl-1-amino]-2-[1H-indole-4,7-dione]prop-β-en-α-ol (E.O. 51)

A similar synthesis procedure has been applied as for the synthesis of the precursor of indoloquinone E.O. 47 (Example 26)

Yield: 74%; dark purple crystals.

M.p.: 208°–210° C.

IR (KBr): 3100–3500 (NH and OH), 1650 (quinone C=O), 1590 (quinone C=C).

$^1$NMR δ(DMSO-d$_6$): 8.45–8.55 (m, 1H, py-H), 7.7–7.85(m, 1H, py-H), 7.2–7.45 (m, 3H, py-H and NH), 6.4–6.6 (m, 2H, CH=CHCH$_2$—), 5.17 (s, 1H, H-6), 5.04 and 4.77 (m, 1H, OH), 4.56 (d, 2H, ArCH$_2$—), 4.2 (m, 2H, CH=CHCH$_2$), 3.92 (s, 3H, NCH$_3$), 3.45–3.6 (m, 2H, CH$_2$NH), 3.04 [t, 2H, J=7 Hz, —CH$_2$—py].

FD MS: m/e 367 (M+).

EXAMPLE 29

3-Acetoxymethyl-1-methyl-5-[2-pyridylethyl-1-amino]-2-[1H-indole-4,7-dione]prop-β-en-α-yl acetate (E.O. 52)

A similar synthesis procedure has been applied as for the synthesis of indoloquinone E.O. 48 (Example 26).

Yield: 86%; purple crystals.

M.p.: 156°–157° C.

IR (CHCl$_3$): 3300 (NH), 1730 (ester C=O), 1660 (quinone C=O), 1590 (quinone C=C).

$^1$NMR δ(CDCl$_3$): 8.55–8.6 (m, 1H, py-H), 7.55–7.65 (m, 1H, py-H), 7.1–7.2 (m, 2H, py-H), 6.4–6.6 (m, 2H, CH=CHCH$_2$— and NH), 6.07 (dt, 1H, J=16.0 Hz and J=5.9 Hz, CH=CHCH$_2$—), 5.24 (s, 1H, H-6), 5.22 (s, 2H, ArCH$_2$—), 4.73 (dd, 2H, J=5.9 and J=1.2 Hz, CH=CHCH$_2$), 3.96 (s, 3H, NCH$_3$), 3.5–3.6 (m, 2H, CH$_2$NH), 3.09 [t, 2H, J=6.6 Hz, —CH$_2$—py], 2.10 and 2.04 (s, 3H, —COCH$_3$.

FD MS: m/e 451 (M+).

EXAMPLE 30

3-Acetoxymethyl-1-methyl-5-propyleneamino-2-[1H-indole-4,7-dione]-prop-β-en-α-yl acetate (E.O. 53)

Indoloquinone E.O. 53 has been synthesized from compound E.O. 8 using the same synthesis procedure as has been described for compound E.O. 47 (Example 26 B).

Yield: 70%; purple crystals.
M.p.: 143°–145° C. (MeOH).
IR (CHCl$_3$): 1735 (ester C=O), 1665 (quinone C=O), 1585 (quinone C=C).
$^1$NMR δ(CDCl$_3$): 6.51 (dt, 1H, J=16.1 Hz and J=1.3 Hz, CH=CHCH$_2$—), 6.12 (dt, 1H, J=16.1 Hz and J=5.8 Hz, CH=CHCH$_2$—), 5.79 (s, 1H, H-6), 5.27 (s, 2H, ArCH$_2$—), 4.76 (dd, 2H, J=5.8 and J=1.3 Hz, CH=CHCH$_2$), 3.94 (s, 3H, NCH$_3$), 2.25–2.4 (m, 1H, CHCH$_3$), 2.05–2.20 (m, 6H, —COCH$_3$ and CH$_2$N), 1.42 (d, 3H, J=5.5 Hz, CHCH$_3$).

BIOLOGICAL DATA

(a) In vitro Activity Experiments

The indoloquinones II (formula II) have been tested in respect of their cytotoxic activity against L1210 cells and R-1 cells (Rhabdomyosarcoma Cells) in a bioliquid assay at the department of oncology of the Free University of Amsterdam (Table I). In addition to this seven compounds (E.O. 1, E.O. 2, E.O. 4, E.O. 7, E.O. 9, E.O. 16 and E.O. 17) have been tested on L1210 activity in a clonogenic assay at TNO, Rijswijk. Further, the lowest active doses of the compounds E.O. 1, E.O. 2, E.O. 4 and E.O. 9 have been determined at TNO Rijswijk, according to the method described by Lamberts et al. [Oncology, 40, 301 (1983)]. (Table II). Eight indoloquinones (E.O. 1, E.O. 2, E.O. 4, E.O. 4A, E.O. 8, E.O. 9, E.O. 33 and E.O. 35) have been tested in a panel of five human tumour lines (TNO Rijswijk; Table III). From the latter group three indoloquinones (E.O. 1, E.O. 4 and E.O. 9) have been selected for a cytotoxicity study, involving five slowly growing human tumour lines (University of Freiburg; Table IV).

(i) Determination of the R-1 Activity (Bioliquid Assay)

For the determination of the R-1 activity, Rhabdomyosarcoma cells were brought into Falcon multiwells (growth area: 9.6 cm$^2$) (~10$^6$ cells per dish) containing 3 ml of Dulbecco's medium supplemented with 10% Foeto Calf Serum (FCS). When the cells have become attached to the polymeric support forming a monolayer (after about 16 hours), they were incubated at 37° C. in an atmosphere of 5% CO$_2$ in humidified air with the compound to be tested (in the appropriate concentration) dissolved in the same medium. Thereupon the drug solution was removed and the cells were covered with fresh medium. After 48 hours the cells were trypsinized and counted on a Sysmex microcell counter (CC110).

TABLE I

IN VITRO ACTIVITY DATA (RHABDOMYOSARCOMA/L1210) OF THE INDOLOQUINONES II

| COMP. | R$_2$ | R$_3$ | R$_5$ | X$_1$ | X$_2$ | ID-50 (μg/ml) R-1 | ID-50 (μg/ml) L1210 |
|---|---|---|---|---|---|---|---|
| E.O. 1 | OCH$_3$ | H | CH$_3$ | OAc | OAc | 2.3 | 2.3 |
| E.O. 1A | OCH$_3$ | H | CH$_3$ | CH | OAc | 3.2 | 2.8 |
| E.O. 1B | OCH$_3$ | H | CH$_3$ | OAc | CH | 0.05 | 0.9 |
| E.O. 2 | OCH$_3$ | H | CH$_3$ | OCOOCH$_3$ | OCOOCH$_3$ | 0.4 | 0.5 |
| E.O. 3 | OCH$_3$ | H | CH$_3$ | OCONH$_2$ | OCONH$_2$ | >10 | 8 |
| E.O. 4 | —N⟨ (azetidinyl) | H | CH$_3$ | OAc | OAc | 0.025 | 1.6 |
| E.O. 4A | —N⟨ (azetidinyl) | H | CH$_3$ | OAc | CH | 0.02 | 0.15 |
| E.O. 5 | NHCH$_2$CH$_2$CH | H | CH$_3$ | OAc | OAc | >10 | >10 |
| E.O. 6 | NHCH$_2$CHCHCH$_2$CH | H | CH$_3$ | OAc | OAc | >10 | >10 |
| E.O. 7 | OCH$_3$ | H | CH$_3$ | CH | CH | 4.2 | 0.5 |
| E.O. 8 | —N⟨CH$_3$ | H | CH$_3$ | CH | CH | 7.6 | 0.5 |
| E.O. 9 | —N⟨ (azetidinyl) | H | CH$_3$ | CH | CH | 0.003 | 0.46 |
| E.O. 10 | OCH$_3$ | H | CH$_3$ | OCH$_3$ | OCONHCH$_2$CH$_2$Cl | >10 | >10 |
| E.O. 11 | —N(piperidinyl)-OH | H | CH$_3$ | CH | CH | >10 | >10 |
| E.O. 12 | —N(morpholinyl)O | H | CH$_3$ | CH | CH | >10 | 3.8 |

TABLE I-continued

IN VITRO ACTIVITY DATA
(RHABDOMYOSARCOMA/L1210) OF THE
INDOLOQUINONES II

| COMP. | R₂ | R₃ | R₅ | X₁ | X₂ | ID-50 (μg/ml) R-1 | L1210 |
|---|---|---|---|---|---|---|---|
| E.O. 13 | OCH₃ | H | CH₃ | | OCONHCH₂CH₂Cl | 1.1 | 10 |
| E.O. 15 | NHC₆H₅ | H | CH₃ | CH | CH | — | 0.7 |
| E.O. 16 | OCH₃ | H | C₄H₉ | CH | CH | — | — |
| E.O. 17 | −N | H | C₄H₉ | CH | CH | — | — |
| E.O. 18 | OCH₃ | CH₃ | CH₃ | CH | CH | 2.2 | 2.4 |
| E.O. 19 | −N | CH₃ | CH₃ | CH | CH | 0.1 | 2.0 |
| E.O. 33 | OCH₃ | CH₃ | CH₃ | OAc | OAc | 2.2 | 3.6 |
| E.O. 35 | −N | CH₃ | CH₃ | OAc | OAc | 0.3 | 0.55 |
| E.O. 36 | OCH₃ | H | CH₃ | | OCOC₆H₅ | 2.6 | 0.7 |
| E.O. 37 | OCH₃ | H | CH₃ | | OCONHC₄H₉ | 6.5 | >10 |
| E.O. 38 | OCH₃ | H | CH₃ | | OCONHC₆H₅ | 8.5 | >10 |
| E.O. 39 | OCH₃ | H | CH₃ | NHC₆H₅ | OAc | 1.0 | 10 |
| E.O. 41 | OCH₃ | H | CH₃ | H | OAc | >10 | >10 |
| E.O. 47 | NHCH₂CH₂(CH₃)₂ | H | CH₃ | OAc | OAc | 4.4 | >10 |
| E.O. 48 | NHCH₂CH₂(CH₃)₂ | H | CH₃ | OAc | CH | >10 | >10 |
| E.O. 51 | 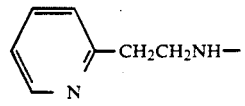—CH₂CH₂NH— | H | CH₃ | CH | CH | 4.5 | >10 |
| E.O. 52 | 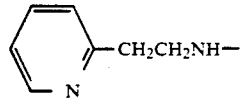—CH₂CH₂NH— | H | CH₃ | OAc | OAc | 3.3 | >10 |
| E.O. 53 | −N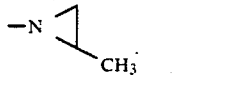CH₃ | H | CH₃ | OAc | OAc | 1.4 | 3.4 |
| E.O. 56 | NHC₂H₅ | H | CH₃ | CH | CH | >10 | 5.1 |
| E.O. 58 | NHC₂H₅ | H | CH₃ | OAc | OAc | >10 | >10 |
| E.O. 59 | NHC₂H₅ | H | CH₃ | OAc | CH | >10 | >10 |
| E.O. 60 | −N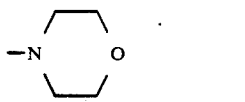O | H | CH₃ | OAc | OAc | 3.3 | >10 |
| E.O. 62 | 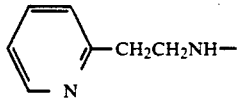—CH₂CH₂NH— | H | CH₃ | OAc | CH | >10 | >10 |
| E.O. 64 | OCH₃ | H | CH₃ | SCSN(Et)₂ | OAc | — | — |
| MMC | NH₂ | | | | | 0.03 | 0.05 |

*Seven indoloquinones.E.O. 1, E.O. 2, E.O. 4, E.O. 7, E.O. 9, E.O. 16, and E.O. 17, have been tested on L1210 activity in a clonogenic assay at TNO Rijswijk. The ID-values (μg/ml) amounted respectively: 2.5, 3.7, <<1, 2.2, 0.8, 0.9 and 0.3 μg/ml.

The para-indoloquinones together with mitomycin C were tested on their activity against R-1 cells. The results are given in Table I.

(ii) Determination of L1210 Activity (Bioliquid Assay)

For this purpose, L1210 cells were grown, as suspension, in Falcon multi-wells (growth area: 9.6 cm²) using RPMI supplemented with 15% FCS and 2-mercaptoethanol (60 μmol) as medium. In this medium, the cells were continuously incubated with the compound to be tested at 37° C. in an atmosphere of 5% CO₂ in humidified air for 48 hours. Thereupon they were counted on a Sysmex microcell counter (CC110). Test results are also given in Table I.

(iii) Determination of the L1210 Activity (Clonogenic Assay)

The L1210 clonogenic assay used was an improved variant of the method described earlier by H. MARTIN et al. [Cancer Chemother., Rep., 51 451 (1967)] and L. M. van Putten et al. [Cancer Treat. Rep., 60, 373 (1976)] for the growth into colonies of L1210 cells in a soft agar medium. From a suspension culture ~100 L1210 Cells (0.1 ml) were plated into 3.5 mm culture dishes (Falcon), containing 1 ml of soft agar growth medium and the compound to be tested in appropriate concentrations. The soft agar growth medium consisted of Dulbecco medium supplemented with 15.8% horse serum, 60 μmol 2-mercapto-ethanol, 20 mg/ml L-asparagine and 0.3% bacto agar (Difco).

The culture dishes were incubated at 37° C. in an atmosphere of 1% $CO_2$ in humidified air for 8 days. After this period of continuous drug exposure, colonies were counted and dose-effect curves were made. From these ID-50 values were calculated which are also given in Table I.

(iv) Determination of Lowest Active Dose (L1210 Cells; Bioliquid Assay)

The lowest active doses for the compounds E.O. 1, E.O. 2, E.O. 4 and E.O. 9 were determined according to the method described by Lamberts et al. [Oncology, 40, 301 (1983)]. In this method, L1210 cells were grown in a series of wells in a culture medium and in the presence of the compound to be tested, as in the determination of L1210 activity in a bioliquid assay reported above, but the compound was present in respective wells in a different concentration, the concentrations extending over an appropriate range. After a suitable incubation period, the lowest active dose for the compound in question was determined by comparing the diameter of each of the precipitation spots with that of a control containing only the culture and the cell suspension, a smaller diameter indicating growth inhibition (Table II).

TABLE II

| COMPOUND | LOWEST ACTIVE DOSE (LAD) (L1210; BIOLIQUID ASSAY) | |
|---|---|---|
| | LAD 1 (ng/ml) | LAD 2[a] (ng/ml) |
| E.O. 1 | 1024–2048 | 1024–2048 |
| E.O. 2 | 1024–2048 | 1024–2048 |
| E.O. 4 | 32–64 | 64 |
| E.O. 9 | 512–1024 | 1024 |

[a]LAD 2 refers to a duplicate experiment.

TABLE IA

IN VITRO ACTIVITY OF THE PARA-INDOLOQUINONE DIESTERS

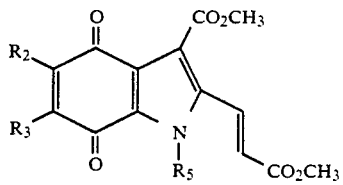

| COMP. | $R_2$ | $R_3$ | $R_5$ | ID-50 (μg/ML) R-1 | L1210 | $E_{\frac{1}{2}}$ (mV)* |
|---|---|---|---|---|---|---|
| E.O. 14 | $OCH_3$ | H | $CH_3$ | >10 | 0.8 | −243 |
| E.O. 29 | $OCH_3$ | H | H | 4.9 | 2.2 | −211 |
| E.O. 32 | $OCH_3$ | $CH_3$ | $CH_3$ | >10 | 3.5 | |
| E.O. 23 | $NHCH_2CHCHCH_2CH$ | H | $CH_3$ | >10 | >10 | −343 |
| E.O. 57 | $NHC_2H_5$ | H | $CH_3$ | 3.2 | 1.4 | |
| E.O. 55 | —N(morpholino) | H | $CH_3$ | 8.9 | 1.4 | −240 |
| E.O. 24 | CH | H | $CH_3$ | >10 | >10 | −299 |
| E.O. 22 | —N(aziridinyl) | H | $CH_3$ | 0.5 | 0.01 | −179 |
| E.O. 34 | —N(aziridinyl) | $CH_3$ | $CH_3$ | 2.8 | 2.7 | −239 |
| E.O. 28 | —N(2-methylaziridinyl) | H | $CH_3$ | 5.7 | 2.2 | −171 |

*The halve wave reduction potentials ($E_{\frac{1}{2}}$) have been determined at the Pharmaceutical Laboratory of University of Utrecht. Only the first (quinone) reduction potential has been given.

The in vitro L1210 and R-1 activities of the indoloquinones (formula III), were also determined in the bioliquid assays as described above. The ID-50 values for these compounds are given in Table IA.

(V) Determination of the in Vitro Activity Against a Panel of Five Human Tumour Lines (TNO Rijswijk: Table III)

Compounds E.O. 1, E.O. 2, E.O. 4, E.O. 4A, E.O. 8, E.O. 9, E.O. 22, E.O. 33, and E.O. 35 were tested for their activity against five human tumour cell lines at the Radiobiological Institute TNO Rijswijk.

The new in vitro prescreen uses human tumour clones; it was set up by Dr. P. Lelieveld at TNO Rijswijk and comprises testing compounds in a bioliquid assay for their cytostatic activity against the following five human tumour lines:

Cells: the human tumour cells are maintained in Dulbecco's medium supplemented with 10 percent foetal calf serum.

A, T and Z cell suspensions: $5 \cdot 10^4$ cells/ml
M and W cell suspensions: $10^5$ cells/ml.

The cells were grafted into 16 mm wells for 48 hours (0.5 ml cell suspension per well was used).

Drugs: the compound to be tested was dissolved in appropriate concentrations in a mixture of Hepes-buffered Hanks' balanced salt solution and ethanol. The drug solutions (0.05 ml) were added to the different wells. The final ethanol concentration in each well was less than one percent.

TABLE III

IN VITRO ACTIVITY: PANEL OF 5 HUMAN TUMOUR LINES (TNO, RIJSWIJK)

| | A 204 | | | | MCF-7 | | | | T 24 | | | |
|---|---|---|---|---|---|---|---|---|---|---|---|---|
| | Dose of drug under test = µg/ml | | | | | | | | | | | |
| | 0.01 | 0.1 | 1.0 | 10 | 0.01 | 0.1 | 1.0 | 10 | 0.01 | 0.1 | 1.0 | 10 |
| E.O. 1 | − | − | ± | + | − | − | − | + | − | − | ± | |
| E.O. 2 | − | − | − | + | − | − | − | + | − | − | − | + |
| E.O. 4 | − | − | + | + | − | − | ± | + | − | − | + | + |
| E.O. 4A | − | − | + | + | − | − | ±/+ | + | − | − | + | + |
| E.O. 8 | − | − | − | ± | − | − | − | − | − | − | − | ± |
| E.O. 9 | − | + | + | + | − | + | + | + | − | + | + | + |
| E.O. 33 | − | − | − | + | − | − | − | ± | − | − | − | + |
| E.O. 35 | − | − | − | ±/+ | − | − | − | ± | − | − | − | ± |
| E.O. 22 | − | − | + | | − | − | ± | | − | − | + | |
| MMC | − | ± | + | + | − | − | ± | + | − | −/± | ±/+ | + |
| Cisplatin | − | − | ± | + | − | − | − | ± | − | − | −/± | + |
| Methotrex. | ± | + | + | + | − | − | − | − | −/± | ±/+ | ±/+ | ±/+ |
| Vinblast. | −/± | ± | | | ±/+ | ±/+ | + | + | ± | + | | |
| Vincrist. | ± | ± | | | ±/+ | ±/+ | | | − | + | | |

| | WiDr | | | | IgR-37 | | | |
|---|---|---|---|---|---|---|---|---|
| | Dose of drug under test = µg/ml | | | | | | | |
| | 0.01 | 0.1 | 1.0 | 10 | 0.01 | 0.1 | 1.0 | 10 |
| E.O. 1 | − | − | − | + | − | − | ± | + |
| E.O. 2 | − | − | − | + | − | − | − | + |
| E.O. 4 | − | − | ± | + | − | − | + | + |
| E.O. 4A | − | − | + | + | − | ± | + | + |
| E.O. 8 | − | − | − | −/± | − | − | − | + |
| E.O. 9 | − | + | + | + | + | + | + | + |
| E.O. 33 | − | − | − | −/± | − | − | − | + |
| E.O. 35 | − | − | − | ± | − | − | ± | + |
| E.O. 22 | − | − | ± | | − | − | + | |
| MMC | − | − | ± | + | − | ±/+ | + | + |
| Cisplatin | − | − | − | + | − | − | −/± | + |
| Methotrex. | − | −/± | −/± | −/± | − | −/± | ± | ± |
| Vinblast | + | + | + | + | + | + | | |
| Vincrist. | + | + | | | + | + | | |

A: A 204 cells; rhabdomyosarcoma
M: MCF-7 breast cancer cells, hormone sensitive, oestrogen receptor-positive [See: G. J. Goldenberg and E. K. Froese, Cancer Res., 42, 5147 (1982)]
T: T 24 cells; bladder carcinoma
W: WiDr cells; colon tumour [See: P. Noguchi et al., In Vitro, 15, 401 (1979)]
Z: IgR-37 cells melanoma To substantiate the new TNO prescreen, the following applies:

MCF-breast cancer cells are routinely used to determine hormone sensitivity

The WiDr tumour line is presently under investigation as one of the colon tumour cell lines for the new in vitro screening panel at the NCI.

After a continuous exposure to the drugs to be tested and to Adriamycin in '24 well tissue culture clusters, type 3524 (Costar)', the remaining cells are fixed and stained. Using increasing drug concentrations the inhibiting concentration can be estimated qualitatively.

The experiments were carried out as follows:

The cells were continuously incubated with the compound under test at 37° in an atmosphere of 10 percent $CO_2$ in humidified air for about 72 hours.

Determination of the inhibiting dose: the cells were fixed and stained with a solution of crystal violet in methanol/formaldehyde.

Scoring:
−no inhibition of cell growth
+total cell-kill

High and selective in vitro toxicity effects have been observed for some indoloquinones in the TNO panel of human tumour lines (See: Table III). Adriamycin was used as the reference compound: comparisons have also been made against other cytostatics including mitomycin C.

TABLE IV

COLONY INHIBITION: IN VITRO, CONTINUOUS DRUG EXPOSURE

| | DOSE (μg/ml) | | | | | | | | |
|---|---|---|---|---|---|---|---|---|---|
| | E.O. 9 | | | E.O. 4 | | | E.O. 1 | | |
| TUMOUR TYPE | 0.01 | 0.1 | 1.0 | 0.001 | 0.01 | 0.1 | 0.01 | 0.1 | 1.0 |
| Colon 1 | 51− | 47+ | 9+++ | 51− | 56− | 56− | 108− | 37+ | 21++ |
| Colon 2 | 136− | 20++ | 1+++ | 86− | 70− | 11++ | 71− | 24++ | 3+++ |
| Lung | 0+++ | 0+++ | 0+++ | 64− | 8+++ | 0+++ | 48+ | 4+++ | 0+++ |
| Mammary | 38+ | 2+++ | 0+++ | 95− | 46+ | 0+++ | 99− | 0+++ | 0+++ |
| Renal | 123− | 8+++ | 0+++ | 88− | 88− | 41+ | NE | 68− | 0+++ |

*Inhibition of colony formation treated/control (T/C)
**T/C: − ≧50; + 30-50; ++ 10-30; +++ <10

(VI) Determination of the in Vitro Activity Against Five Slowly Growing Human Tumour Lines (University of Freiburg: Table IV)

Three indoloquinones were tested at the University of Freiburg with respect to their in vitro inhibition of colony formation of the following five human tumour cell lines: lung-NSCLC, breast, renal and two colon lines.

At a low concentration of 0.01 μg/ml, E.O. 9 and E.O. 4 were active against the lung cell line. At a concentration of 0.1 μg/ml, activity was seen with all three analogues in several lines (Table IV).

(VII) Electrochemical Properties of the Para-Indoloquinones

Additional evidence for the occurrence of a bioreductive activation mechanism during the cytotoxic action of indoloquinones (II) was obtained via electrochemical studies, which have been carried out at the Pharmaceutical Laboratory of the University of Utrecht.

TABLE V

HALVEWAVE POTENTIALS OF SOME PARAINDOLOQUINONES
E1.2 (mV) at pH = 8 vs Ag/AgCl

| COMPOUND | I | II | III | IV |
|---|---|---|---|---|
| E.O. 1 | −367 | | −435 | −775 |
| E.O. 6 | −515 | | −600 | −985 |
| E.O. 7 | −367 | | | |
| E.O. 8 | −380 | −780 | | |
| E.O. 9 | −370 | −785 | | |
| E.O. 11 | −430 | | | |
| E.O. 12 | −420 | | | |

The direct current polarogram of indoloquinone E.O. 7 displays a reduction wave representing the reversible reduction of the benzoquinone nucleus. The DC-polarograms of indoloquinones E.O. 1 and E.O. 6, however, are composed of two or more reduction waves, indicating the formation of new electrochemically reducible compounds during the electrochemical reduction, presumably via the elimination of one or both OAc groups (Table V). Similar waves have been observed upon reducing MMC. The latter results have been affirmed by cyclic voltammetric experiments with compound E.O. 6. The shape and size of the reduction and oxidation wave differ considerably. After the first cycle, however, the chemically trapped intermediates afford rather reversible voltammograms.

TABLE VI

THE INFLUENCE OF THE NATURE OF THE SUBSTITUENTS R₂ AND R₃ ON THE ID-50 VALUES

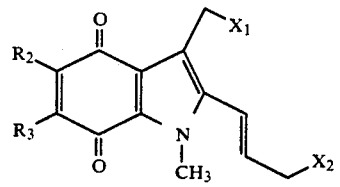

| | | | | | ID-50(μg/ml) | |
|---|---|---|---|---|---|---|
| COMP. | R₂ | R₃ | X₁ | X₂ | R-1 | L1210 |
| E.O. 1 | OCH₃ | H | OAc | OAc | 0.3 | 2.3 |
| E.O. 33 | OCH₃ | CH₃ | OAc | OAc | 2.2 | 3.6 |
| E.O. 60 | 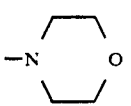 | H | OAc | OAc | 3.3 | >10 |
| E.O. 47 | NHCH₂CH₂(CH₃)₂ | H | OAc | OAc | 4.4 | >10 |

TABLE VI-continued

THE INFLUENCE OF THE NATURE OF THE SUBSTITUENTS $R_2$ AND $R_3$ ON THE ID-50 VALUES

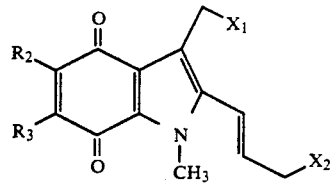

| COMP. | $R_2$ | $R_3$ | $X_1$ | $X_2$ | ID-50(μg/ml) R-1 | L1210 |
|---|---|---|---|---|---|---|
| E.O. 52 | ⟨pyridyl⟩-CH$_2$CH$_2$NH— | H | OAc | OAc | 3.3 | >10 |
| E.O. 58 | NHC$_2$H$_5$ | H | OAc | OAc | >10 | >10 |
| E.O. 5 | NHCH$_2$CH$_2$CH | H | OAc | OAc | >10 | >10 |
| E.O. 6 | NHCH$_2$CHCHCH$_2$CH | H | OAc | OAc | >10 | >10 |
| E.O. 1B | OCH$_3$ | H | OAc | CH | 0.05 | 0.9 |
| E.O. 48 | NHCH$_2$CH$_2$(CH$_3$)$_2$ | H | OAc | CH | >10 | >10 |
| E.O. 62 | ⟨pyridyl⟩-CH$_2$CH$_2$NH— | H | OAc | CH | >10 | >10 |
| E.O. 7 | OCH$_3$ | H | CH | CH | 4.2 | 0.5 |
| E.O. 18 | OCH$_3$ | CH$_3$ | CH | CH | 2.2 | 2.4 |
| E.O. 12 | —N(morpholino) | H | CH | CH | >10 | 3.8 |
| E.O. 11 | —N(piperidinyl-OH) | H | CH | CH | >10 | >10 |
| E.O. 51 | ⟨pyridyl⟩-CH$_2$CH$_2$NH— | H | CH | CH | 4.5 | >10 |
| E.O. 56 | NHC$_2$H$_5$ | H | CH | CH | >10 | 5.1 |

*The compounds in the three different series have been arranged according to the increasing electrondonating properties of the substituents $R_2$ and $R_3$.

It was clear from these experiments that a consecutive chemical reaction occurs after the reduction of the quinone ring, which might be important for the activation in vivo.

(VIII) Correlation of Structural Parameters with in Vitro Cytotoxicity of the Indoloquinones II.

The Influence of the Nature of the Substituents $R_2$ and $R_3$ on the ID-50 Values (Table VI)

The following conclusions can be drawn:
Generally the indoloquinones display a different toxicity against the two cell lines.

The activity decreases considerably upon increasing the electron-donating nature of the $R_2$ and $R_3$ substituents.

The rather high activities (R-1) of indoloquinones E.O. 47 and E.O. 52 may be ascribed to an intramolecular assisted proton abstraction by the additional nitrogen atoms in the reductive activation sequence. Presumably a similar process is also partly responsible for the promising activity of a new C-7 MMC analogue, carrying a —N=CH—(CH$_3$)$_2$ substituent at carbon atom C-7.

The Influence of the Nature of the Leaving Groups $X_1$ and $X_2$ on the ID-50 Values (Table VII).

The main conclusion, which can be drawn from this table is that a reduction of the leaving group abilities of substituents $X_1$ and $X_2$ does increase the ID-50 values. This effect is the most pronounced for the substituent $X_1$ at the C-10 carbon atom.

Striking is the rather high R-1 activity observed for compound E.O. 39. Reduction experiments (H$_2$/PtO$_2$)

have provided evidence for the propensity of the one- or two-electron reduced indoloquinone E.O. 39 to decompose into reactive iminium and quinone methide species (Scheme XII).

TABLE VII

THE INFLUENCE OF THE NATURE OF THE LEAVING GROUPS $X_1$ AND $X_2$ ON THE ID-50 VALUES.

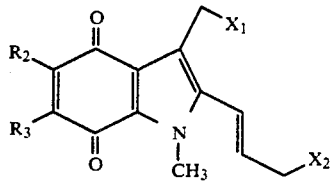

| COMP. | $R_2$ | $R_3$ | $X_1$ | $X_2$ | ID-50($\mu$g/ml) R-1 | L1210 |
|---|---|---|---|---|---|---|
| E.O. 1   | OCH$_3$ | H | OAc      | OAc              | 0.3  | 2.3  |
| E.O. 1A  | OCH$_3$ | H | CH       | OAc              | 3.2  | 2.8  |
| E.O. 1B  | OCH$_3$ | H | OAc      | OH               | 0.05 | 0.9  |
| E.O. 2   | OCH$_3$ | H | OCOOCH$_3$ | OCOOCH$_3$     | 0.4  | 0.5  |
| E.O. 36  | OCH$_3$ | H |          | OCOC$_6$H$_5$    | 2.6  | 0.7  |
| E.O. 37  | OCH$_3$ | H |          | OCONHC$_4$H$_9$  | 6.5  | >10  |
| E.O. 38  | OCH$_3$ | H |          | OCONHC$_5$H$_5$  | 8.5  | >10  |
| E.O. 13  | OCH$_3$ | H |          | OCONHCH$_2$CH$_2$Cl | 1.1 | 10 |
| E.O. 10  | OCH$_3$ | H | OCH$_3$  | OCONHCH$_2$CH$_2$Cl | >10 | >10 |
| E.O. 41  | OCH$_3$ | H | H        | OAc              | >10  | >10  |
| E.O. 39  | OCH$_3$ | H | NHC$_6$H$_5$ | OAc          | 1.0  | 10   |

TABLE VIII

IN VITRO ACTIVITY OF THE BIOREDUCTIVE ALKYLATING AZIRIDINYL INDOLOQUINONES

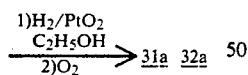

| COMP. | $R_2'$ | $R_3$ | $X_1$ | $X_2$ | ID-50($\mu$g/ml) R-1 | L1210 |
|---|---|---|---|---|---|---|
| E.O. 4   | H      | H      | OAc  | OAc  | 0.025  | 1.6  |
| E.O. 4A  | H      | H      | OAc  | CH   | 0.022  | 0.15 |
| E.O. 9   | H      | H      | CH   | CH   | 0.0034 | 0.46 |
| E.O. 35  | H      | CH$_3$ | OAc  | OAc  | 0.32   | 0.55 |
| E.O. 19  | H      | CH$_3$ | CH   | CH   | 0.12   | 2.0  |
| E.O. 53  | CH$_3$ | H      | OAc  | OAc  | 1.4    | 3.4  |
| E.O. 8   | CH$_3$ | H      | CH   | CH   | 7.6    | 0.48 |
| MMC      |        |        |      |      | 0.03   | 0.05 |

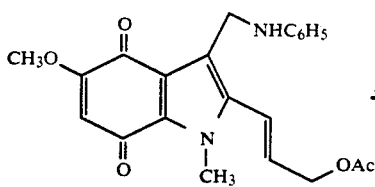

E.O. 39

The in Vitro Activities of the Aziridinyl Indoloquinones (Table VIII: FIG. 1).

Substitution of the methoxy group at the quinone nucleus by an aziridinyl group reduces the ID-50 values—especially in the R-1 series—to a great extent. The presence of the additional alkylation center in this group of indoloquinones has been clearly demonstrated on reducing compound E.O. 4 with Na$_2$S$_2$O$_4$ and simultaneous trapping of the reactive intermediate with N,N-diethyldithiocarbamate-anions (Scheme XIII).

SCHEME XIII

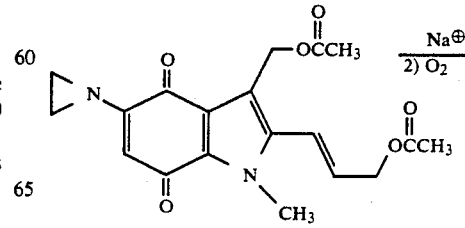

38

-continued
SCHEME XIII

39

The inhibiting doses observed in the R-1 experiments are generally low than those in the L1210 experiments. Introduction of a methyl group either on one of the carbon atoms of the aziridinyl ring or at the C-carbon atom of the indole nucleus, reduces the cytotoxic activities of the indoloquinones considerably.

BIOLOGICAL DATA

(b) In vivo Experiments

(i) Determination of the Acute Toxicity

The acute toxicity experiments were carried out with male C5 Black/Rij X CBA/Rij F1 hybrid mice at TNO, Rijswijk. The drugs were administrated IP as suspensions in carboxymethyl cellulose (2%) as a single dose at the first day. The results are given in Table IX below.

(ii) In vivo L1210 Experiments

The in vivo L1210 experiments were carried out in male Balb/c X DBA.2 F1 hybrid mice at TNO, Rijswijk.

TABLE IX
ACUTE TOXICITY AND IN VIVO L1210 EXPERIMENTS (TNO,RIJSWIJK)

| COMPOUND | DOSES (MG/KG) | % T/C | LD-50 (MG/KG) |
|---|---|---|---|
| E.O. 1 | 10, 15, 25 | 100 | 10-30 |
| E.O. 2 | 30 | 100 | 30-100 |
|  | 40 | 113 |  |
|  | 60 | 100 |  |
|  | 80 | tox. |  |
| E.O. 4 | 4, 8, 12 | 100 | −30 |
|  | 15 | tox. |  |
|  | 20 | 100 |  |
|  | 25, 30 | tox. |  |
| E.O. 7 | 100, 125, 160, 200 | 89 | >100 |
|  | 250 | tox. |  |
| E.O. 9 | 2 | 144 | 10 |
|  | 4 | 100 |  |
|  | 6, 8, 10 | tox. |  |
| E.O. 16 | 80 | 89 | 80 |
|  | 100 | 100 |  |
| E.O. 17 | 50, 60 | 100 | 50-80 |
| MMC[a] | 4 | 200 | 8 |
|  | 5 | 175 |  |
|  | 6 | 175 |  |

[a]Remers et al., J. Med. Chem. 26 16 (1983): max. effect (% T/C) 124-153 (3-6 mg/kg): a range based on numerous determinations.

In these experiments also, the drugs were administered IP as suspensions in carboxymethyl cellulose (2) as a single dose at the first day. The results are also given in Table IX.

(iii) In vivo P388 Experiments

These experiments were carried out at the Institute Jules Bordet, Brussels, on CDF, female mice. The mice were inoculated intraperitoneally (IP) with 1×10^6 P 388 tumour cells. After 24 hours, the compounds were administrated as suspensions in "Tween-80" or using saline as vehicle. Six mice were used at each dose of the compound, given on days 1 to 5 and eighteen control mice were injected with saline.

Two indoloquinones (E.O. 4 and E.O. 35) showed reproducible and marginal activity at the optimal dose (T/C approx.: 130%) [Table X].

TABLE X
IN VIVO P388 EXPERIMENTS (NCI; BRUSSELS)

| COMPOUND | DOSES (MG/KG) | MAX T/C (%) |
|---|---|---|
| E.O. 1 | 75 | 105 |
| E.O. 2 | 10 | 120 |
| E.O. 4 | 10 | 135 |
| E.O. 4A | 100 | 120 |
| E.O. 9 | 1.5 | 106 |
| E.O. 35 | 400 | 131 |

(iv) Tumour Growth Inhibition of Human Tumour Xenografts by Indoloquinone E.O. 9 in Nude Mice Based on the results obtained during the in vitro experiments indoloquinone E.O. 9 was selected for an extended in vivo study. The activity of this compound has been determined in four human tumour xenografts transplanted in nude mice.

The xenograft experiments have been carried by Dr. H. H. Fiebig of the University of Freiburg [Lung-NSCLC (LXGF) line, Renal line, Breast line; See: H. H. Fiebig et al., Behring Inst. Mitt., 74 343] and by Dr. E. Boven of the Free University Hospital Amsterdam [Ovarian (MRI-H-207) line; See: E. Boven et al., Cancer Res., 45, 86 (1985) and E. Boven et al., Eur. J. Clin. Oncol., 21, 1253 (1985)].

Lung-NSCLC (LXFG) line:

(This is the same line as evaluated in vitro: Table IV).

The tumour was transplanted s.c. and E.O. 9 was administrated i.v. on days 14 and 21 after transplantation at a dose of 4 and 6 mg/kg.

An optimal growth inhibition of 42% and a specific growth delay of 1.03 was reached (FIG. II).

Renal line (RXF 423):

(This is the same line as evaluated in vitro: Table IV).

The tumour was transplanted s.c. and E.O. 9 was administrated i.v. on days 22 and 29 after transplantation at a dose of 4 and 6 mg/kg. No significant growth inhibition was achieved (FIG. III).

Breast line:

(Due to low take in vivo this is not the same line as evaluated in vitro).

The tumour was transplanted s.c. and E.O. 9 was administrated i.v. on days 46 and 53 after transplantation at a dose of 4 and 6 mg/kg.

An optimal growth inhibition of 51% was reached (FIG. IV).

Ovarian (MRI-H-207) line:

These experiments have been carried out by Dr. E. Boven of the Free University Hospital, Amsterdam.

Materials and Methods

Mice: C57B1 athymic (nu/nu) female mice, 8 to 10 weeks of age were used for s.c. bilateral implantation of tumour fragments 2 mm diameter.

Treatment: E.O. 9 was dissolved in saline at a concentration of 0.5 mg/ml prior to administration. Drug doses and schedules were derived from studies in experimental murine tumour systems and from orientation studies in non-tumour-bearing nude mice. Treatment was started i.v. when tumours measured 50–150 mm³. After randomization a group of 6–7 tumour-bearing mice was treated and a group of 5–6 tumour-bearing mice served as control.

Evaluation of efficacy: Tumours were measured twice weekly in three dimensions. Efficacy was expressed as the mean of relative tumour volume in treated animals vs. that in control animals×100 (% T/C). The optimal value was calculated within 35 days after the last injection. Toxic death (dead mice within two weeks after the last injection) were excluded from the evaluation.

MRI-H-207: An undifferentiated adenocarcinoma kindly provided by Dr. A. E. Bogden, Worcester, Mass, with a doubling time of 3–5 days.

TABLE XI

ACTIVITY OF CYTOSTATIC AGENTS IN THE OVARIAN CANCER XENOGRAFT MRI-H-207

| COMPOUND | DOSE (MG/KG) | DAYS OF TREATMENT | T/C % | TOXIC DEATHS |
|---|---|---|---|---|
| E.O. 9 | 5 | 0.7 | 3.8 | 0/7 |
| E.O. 9 | 6 | 0.7 | 2.4 | 1/7 |
| MMC | 5 | 0.7 | CR[a] | 1/7 |
| Cisplatin | 5 | 0.8 | CR | 0/7 |
| Carboplatin | 60 | 0.6 | CR | 0/6 |
| HMM | 150 | 0,2,4,6 | CR | 1/6 |
| CTX | 180 | 0.15 | CR | 2/7 |
| DXR | 10 | 0.7 | CR | 1/6 |
| MTX | 150 | 0,9,16 | 47 | 2/7 |
| 5FU | 60 | 0,6,13,20 | 63 | 0/7 |

[a]CR = complete remission

Results

The tumour was transplanted i.v. at a dose of 5 and 6 mg/kg q8d×2. An optimal growth inhibition of 98% was reached (FIG. V; Table XI). Comparative activity of clinical relevant compounds in ovarian cancer are given as well in Table XI.

We claim:

1. Indoloquinone compounds of the general formula:

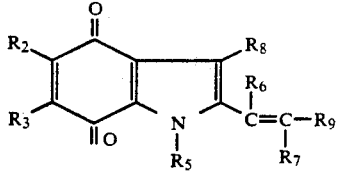

(I)

where $R_2$ and $R_3$ are in each case, hydrogen, halogen, a ($C_1$–$C_6$) alkyl group, a ($C_1$–$C_6$) alkoxy group or a phenoxy group, a ($C_1$–$C_6$) alkylthio group or a phenylthio group, a primary or a secondary amino group, hydroxy group or an amino group;

$R_5$ is hydrogen, a hydroxy group, a ($C_1$–$C_6$) alkoxy group, or a ($C_1$–$C_6$) alkyl group;

$R_6$ and $R_7$ are in each case hydrogen, halogen, or a ($C_1$–$C_6$) alkyl group;

$R_8$ is a group —$CH_2X_1$, or a group —$CO_2R_{10}$ where $R_{10}$ is hydrogen or a ($C_1$–$C_6$) alkyl group;

$R_9$ is a group —$CR_{11}R_{12}X_2$ where $R_{11}$ and $R_{12}$ are in each case hydrogen or a ($C_1$–$C_6$) alkyl group; or a group —$CO_2R_{13}$ where $R_{13}$ is hydrogen or a ($C_1$–$C_{12}$) alkyl group; and $X_1$ and $X_2$ (when present) may be the same or different and are hydrogen, or groups selected from OR, —OC=OR, —OCO$_2$R, —OC=ONRR, —SCO$_2$R, and —NRR where R is hydrogen, a ($C_1$–$C_{12}$) alkyl group, or a phenyl group, —OSOR$_{14}$, —OSO$_2$R$_{14}$ and OP(OR$_{14}$)$_2$ where R$_{14}$ is hydrogen, a ($C_1$–$C_{12}$) group, or a phenyl group;

and pharmaceutically acceptable salts thereof.

2. Indoloquinone compounds as claimed in claim 1 of the general formula:

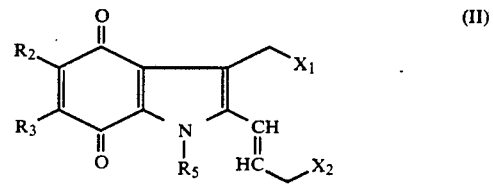

(II)

where $R_3$ is a methoxy group —$OCH_3$, or a primary or secondary amino group, $R_2$ is hydrogen or a methyl group; $R_5$ is a methyl or butyl group; and $X_1$ and $X_2$ are selected from hydrogen, —OH, —OAc, —OCOOCH$_3$, —CONH$_2$, —O-CONHCH$_2$CH$_2$Cl, —OCOC$_6$H$_5$, —OCOC$_4$H$_9$, —NHC$_6$H$_5$, SC=OOC$_2$H$_5$ and —OCH$_3$ groups and may be the same or different and pharmaceutically acceptable salts thereof.

3. Indoloquinone compounds of the general formula:

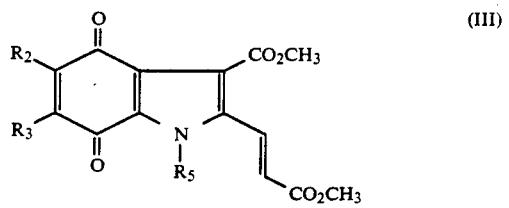

(III)

where $R_2$ and $R_3$ are in each case, hydrogen, halogen, a ($C_1$–$C_6$) alkyl group, a ($C_1$–$C_6$) alkoxy group or a phenoxy group, a ($C_1$–$C_6$) alkylthio group or a phenylthio group, a primary or a secondary amino group, hydroxy group or an amino group; $R_5$ is hydrogen, a hydroxy group, a ($C_1$–$C_6$) alkoxy group, or a ($C_1$–$C_6$) alkyl group;

and pharmaceutically acceptable salts thereof.

4. A method for achieving a cytostatic effect in a patient in need of such treatment comprising administering a cytostatically-effective amount of a compound of claim 1 or claim 2.

* * * * *